(12) United States Patent
Shenoy

(10) Patent No.: US 9,610,251 B2
(45) Date of Patent: Apr. 4, 2017

(54) PHARMACEUTICAL COMPOSITIONS FOR SUBSTITUTED QUINAZOLINONES

(71) Applicant: Resverlogix Corp., Calgary (CA)

(72) Inventor: Narmada R. Shenoy, Sunnyvale, CA (US)

(73) Assignee: Resverlogix Corp., Calgary, Alberta (CA)

( * ) Notice: Subject to any disclaimer, the term of this patent is extended or adjusted under 35 U.S.C. 154(b) by 0 days.

(21) Appl. No.: 13/665,147

(22) Filed: Oct. 31, 2012

(65) Prior Publication Data

US 2013/0108672 A1     May 2, 2013

Related U.S. Application Data

(60) Provisional application No. 61/554,090, filed on Nov. 1, 2011.

(51) Int. Cl.
*A61P 35/00*     (2006.01)
*A61K 9/48*     (2006.01)
*A61K 31/517*     (2006.01)

(52) U.S. Cl.
CPC .......... *A61K 9/4858* (2013.01); *A61K 9/4866* (2013.01); *A61K 31/517* (2013.01)

(58) Field of Classification Search
CPC ..... A61K 31/517; A61K 31/47; A61K 9/4858
USPC ...................... 424/133, 462; 514/282, 166.31
See application file for complete search history.

(56) References Cited

U.S. PATENT DOCUMENTS

| | | |
|---|---|---|
| 2,065,593 A | 12/1936 | Lubs |
| 2,065,900 A | 12/1936 | Laska et al. |
| 2,071,329 A | 2/1937 | Brown |
| 3,251,837 A | 5/1966 | Holland |
| 3,600,394 A | 8/1971 | Coyne et al. |
| 3,773,946 A | 11/1973 | Creger |
| 3,930,024 A | 12/1975 | Creger |
| 3,965,128 A | 6/1976 | Fürst et al. |
| 4,613,593 A | 9/1986 | Yamatsu et al. |
| 4,689,344 A | 8/1987 | Bar-Tana |
| 4,711,896 A | 12/1987 | Bar-Tana et al. |
| 4,825,005 A | 4/1989 | Frey et al. |
| 5,098,903 A | 3/1992 | Magarian et al. |
| 5,124,337 A | 6/1992 | Dugar et al. |
| 5,126,351 A | 6/1992 | Luzzio et al. |
| 5,244,904 A | 9/1993 | Nagase et al. |
| 5,280,024 A | 1/1994 | Bolland et al. |
| 5,354,749 A | 10/1994 | Dressel et al. |
| 5,407,942 A | 4/1995 | Dressel et al. |
| 5,409,930 A | 4/1995 | Spada et al. |
| 5,446,071 A | 8/1995 | Grese |
| 5,474,994 A | 12/1995 | Leonardi et al. |
| 5,480,883 A | 1/1996 | Spada et al. |
| 5,539,119 A | 7/1996 | Nagase et al. |
| 5,576,322 A | 11/1996 | Takase et al. |
| 5,595,974 A | 1/1997 | Tomaru |
| 5,693,652 A | 12/1997 | Takase et al. |
| 5,707,987 A | 1/1998 | Nakagawa et al. |
| 5,733,913 A | 3/1998 | Blankley et al. |
| 5,756,344 A | 5/1998 | Onda et al. |
| 5,756,544 A | 5/1998 | Bisgaier et al. |
| 5,756,736 A | 5/1998 | Arzeno et al. |
| 5,756,763 A | 5/1998 | Takeuchi et al. |
| 5,763,414 A | 6/1998 | Bok et al. |
| 5,783,577 A | 7/1998 | Houghten et al. |
| 5,792,461 A | 8/1998 | Bok et al. |
| 5,792,902 A | 8/1998 | Benoit et al. |
| 5,798,344 A | 8/1998 | Kuroki et al. |
| 5,801,180 A | 9/1998 | Takase et al. |
| 5,817,674 A | 10/1998 | Clemence et al. |
| 5,854,264 A | 12/1998 | Anthony et al. |
| 5,877,208 A | 3/1999 | Bok et al. |
| 5,922,866 A | 7/1999 | Miyata et al. |
| 5,965,556 A | 10/1999 | Takeuchi et al. |
| 6,022,901 A | 2/2000 | Goodman |
| 6,048,903 A | 4/2000 | Toppo |
| 6,054,435 A | 4/2000 | Or et al. |
| 6,133,241 A | 10/2000 | Bok et al. |
| 6,165,984 A | 12/2000 | Bok et al. |
| 6,168,776 B1 | 1/2001 | Klunk et al. |

(Continued)

FOREIGN PATENT DOCUMENTS

| | | |
|---|---|---|
| AU | 719140 B2 | 7/1998 |
| CA | 2104981 A1 | 3/1994 |
| CA | 2345406 A1 | 4/2000 |
| CA | 2815127 A1 | 4/2012 |
| DE | 35 32 279 A1 | 3/1987 |
| DE | 36 01 417 A1 | 7/1987 |
| EP | 0 210 342 A2 | 2/1987 |
| EP | 0 182 213 B1 | 9/1990 |
| EP | 0 407 217 A1 | 1/1991 |
| EP | 0 410 834 A1 | 1/1991 |

(Continued)

OTHER PUBLICATIONS

Varthalis et al.; Title: The action of colloidal silicon dioxide as a glidant for lactose, paracetamol, oxytetracycline and their mixtures, J. Pharm. Pharmac., 1977, 29, pp. 37-40, published 1977.*

Bagul et al.; Title: Current status of Tablet Disintegrants: A review, published Jul. 8, 2006.*

Avicel PH, product information from FMC, downloaded from http://www.fmcbiopolymer.com/Portals/Pharm/Content/Docs.pdf on Aug. 15, 2013 (supplied in OA dated Aug. 16, 2013).*

(Continued)

*Primary Examiner* — Yanzhi Zhang
(74) *Attorney, Agent, or Firm* — Finnegan, Henderson, Farabow, Garrett & Dunner, LLP

(57) ABSTRACT

The present disclosure relates to novel solid pharmaceutical formulations and process for their preparation. The present disclosure also provides, in part, methods of using the pharmaceutical formulations for regulating the expression of apolipoprotein A-I (ApoA-I), and their use for the treatment and prevention of cardiovascular disease and related disease states, including cholesterol- or lipid-related disorders, such as, for example, atherosclerosis.

7 Claims, No Drawings

(56) References Cited

U.S. PATENT DOCUMENTS

| | | |
|---|---|---|
| 6,239,114 B1 | 5/2001 | Guthrie et al. |
| 6,291,456 B1 | 9/2001 | Stein et al. |
| 6,303,629 B1 | 10/2001 | Kun |
| 6,340,759 B1 | 1/2002 | Ueno et al. |
| 6,414,037 B1 | 7/2002 | Pezzuto et al. |
| 6,455,577 B2 | 9/2002 | Bok et al. |
| 6,479,499 B1 | 11/2002 | Kuo et al. |
| 6,482,479 B1 | 11/2002 | Dübal et al. |
| 6,512,161 B1 | 1/2003 | Rouy et al. |
| 6,521,253 B1 * | 2/2003 | Forsman .............. A61K 9/2009 424/464 |
| 6,541,045 B1 | 4/2003 | Charters et al. |
| 6,541,522 B2 | 4/2003 | Inman et al. |
| 6,548,548 B2 | 4/2003 | Campbell et al. |
| 6,613,772 B1 | 9/2003 | Schindler et al. |
| 6,635,642 B1 | 10/2003 | Jackson et al. |
| 6,673,780 B2 | 1/2004 | Dasseux et al. |
| 6,703,422 B2 | 3/2004 | Dasseux et al. |
| 7,087,612 B2 | 8/2006 | Rodriguez Sarmiento et al. |
| 7,173,128 B2 | 2/2007 | Ravichandran et al. |
| 7,244,776 B2 | 7/2007 | Ravichandran et al. |
| 7,846,915 B2 | 12/2010 | Wong et al. |
| 8,053,440 B2 | 11/2011 | Hansen |
| 8,093,273 B2 | 1/2012 | Wong et al. |
| 8,114,995 B2 | 2/2012 | Hansen et al. |
| 8,242,130 B2 | 8/2012 | Wong et al. |
| 8,242,144 B2 | 8/2012 | Wong et al. |
| 8,410,109 B2 | 4/2013 | Wong et al. |
| 8,884,046 B2 | 11/2014 | Lozanov et al. |
| 8,889,698 B2 | 11/2014 | Hansen |
| 8,952,021 B2 | 2/2015 | Hansen |
| 2002/0004608 A1 | 1/2002 | Alig et al. |
| 2002/0025301 A1 | 2/2002 | Haremza et al. |
| 2002/0091263 A1 | 7/2002 | Trova |
| 2003/0064967 A1 | 4/2003 | Luchoomun et al. |
| 2003/0068526 A1 | 4/2003 | Kamatani et al. |
| 2003/0072964 A1 | 4/2003 | Kwong et al. |
| 2003/0171429 A1 | 9/2003 | Chen et al. |
| 2004/0001834 A1 | 1/2004 | Kim et al. |
| 2004/0033480 A1 | 2/2004 | Wong |
| 2004/0058903 A1 | 3/2004 | Takasugi et al. |
| 2004/0097493 A1 | 5/2004 | Chen et al. |
| 2004/0198750 A1 | 10/2004 | Green et al. |
| 2004/0235888 A1 | 11/2004 | Yamamori et al. |
| 2004/0242615 A1 | 12/2004 | Yamamori et al. |
| 2004/0248950 A1 | 12/2004 | Ishizuka et al. |
| 2005/0043300 A1 | 2/2005 | Middleton et al. |
| 2005/0080021 A1 | 4/2005 | Tucker et al. |
| 2005/0080024 A1 | 4/2005 | Tucker et al. |
| 2005/0261319 A1 | 11/2005 | Deuschle et al. |
| 2006/0116364 A1 | 6/2006 | Hamaoka et al. |
| 2007/0099826 A1 | 5/2007 | Wong et al. |
| 2007/0185160 A1 | 8/2007 | Hattori et al. |
| 2007/0218155 A1 | 9/2007 | Kuhrts |
| 2008/0152595 A1 * | 6/2008 | Emigh et al. ................ 424/10.4 |
| 2008/0275069 A1 | 11/2008 | Mizutani et al. |
| 2010/0004448 A1 * | 1/2010 | Hansen et al. ................ 544/289 |
| 2010/0055173 A1 * | 3/2010 | Penhasi et al. .............. 424/452 |
| 2010/0093636 A1 | 4/2010 | Schultz et al. |
| 2010/0137400 A1 | 6/2010 | Karavas et al. |
| 2011/0201608 A1 | 8/2011 | Hoffman et al. |
| 2011/0294807 A1 | 12/2011 | Hansen |
| 2012/0015905 A1 | 1/2012 | Hansen |
| 2012/0040954 A1 | 2/2012 | Hansen |
| 2012/0059002 A1 | 3/2012 | Hansen et al. |
| 2014/0107369 A1 | 4/2014 | Lozanov et al. |
| 2015/0072955 A1 | 3/2015 | Hansen |

FOREIGN PATENT DOCUMENTS

| | | |
|---|---|---|
| EP | 0 258 190 B1 | 11/1991 |
| EP | 0 488 602 A1 | 6/1992 |
| EP | 0 272 455 B1 | 2/1993 |
| EP | 0 375 404 B1 | 2/1994 |
| EP | 0 333 175 B1 | 6/1994 |
| EP | 0 343 499 B1 | 7/1994 |
| EP | 0 409 413 B1 | 8/1994 |
| EP | 0 420 511 B1 | 8/1994 |
| EP | 0 633 022 A2 | 1/1995 |
| EP | 0 330 108 B1 | 12/1995 |
| EP | 0 747 051 A2 | 12/1996 |
| EP | 0 564 350 B1 | 5/1997 |
| EP | 0 643 119 B1 | 4/2000 |
| EP | 1 125 908 A1 | 8/2001 |
| EP | 0 498 723 B1 | 9/2001 |
| EP | 0 607 439 B1 | 1/2002 |
| EP | 0 776 893 B1 | 2/2002 |
| EP | 1 195 378 A1 | 4/2002 |
| EP | 1 277 738 A1 | 1/2003 |
| EP | 1 398 032 A1 | 3/2004 |
| EP | 1 418 164 A1 | 5/2004 |
| EP | 1 426 046 A1 | 6/2004 |
| EP | 1 477 481 A1 | 11/2004 |
| EP | 1 637 523 A1 | 3/2006 |
| EP | 1 757 594 A1 | 2/2007 |
| EP | 1 944 301 A1 | 7/2008 |
| EP | 2 005 941 A2 | 12/2008 |
| FR | 2 244 493 | 4/1975 |
| GB | 472489 | 9/1937 |
| GB | 728767 | 4/1955 |
| GB | 1175808 | 12/1969 |
| GB | 1179019 | 1/1970 |
| GB | 2 292 149 A | 2/1996 |
| IE | 902587 A1 | 7/1990 |
| JP | 6-80656 A | 3/1994 |
| JP | 7-41442 A | 2/1995 |
| JP | 7-61942 A | 3/1995 |
| JP | 7-118241 A | 5/1995 |
| JP | 7-179380 A | 7/1995 |
| JP | 7-233109 A | 9/1995 |
| JP | 7-247289 A | 9/1995 |
| JP | 10-287678 A | 10/1998 |
| JP | 2001-131151 A | 5/2001 |
| JP | 2001-139550 A | 5/2001 |
| JP | 2001-335476 A | 12/2001 |
| JP | 2002-249483 A | 9/2002 |
| JP | 2004-203751 A | 7/2004 |
| JP | 2004-307440 A | 11/2004 |
| WO | WO 91/18901 A1 | 12/1991 |
| WO | WO 92/09374 A1 | 6/1992 |
| WO | WO 92/18123 A2 | 10/1992 |
| WO | WO 92/20642 A1 | 11/1992 |
| WO | WO 92/21661 A1 | 12/1992 |
| WO | WO 93/07124 A1 | 4/1993 |
| WO | WO 93/08174 A1 | 4/1993 |
| WO | WO 94/14763 A1 | 7/1994 |
| WO | WO 95/03277 A1 | 2/1995 |
| WO | WO 95/23150 A1 | 8/1995 |
| WO | WO 96/15128 A2 | 5/1996 |
| WO | WO 96/31206 A2 | 10/1996 |
| WO | WO 97/10221 A1 | 3/1997 |
| WO | WO 97/15308 A1 | 5/1997 |
| WO | WO 97/28118 A1 | 8/1997 |
| WO | WO 97/28132 A1 | 8/1997 |
| WO | WO 97/28134 A1 | 8/1997 |
| WO | WO 97/29106 A1 | 8/1997 |
| WO | WO 97/48694 A1 | 12/1997 |
| WO | WO 98/11438 A1 | 3/1998 |
| WO | WO 98/26127 A1 | 6/1998 |
| WO | WO 98/30530 A1 | 7/1998 |
| WO | WO 98/50370 A1 | 11/1998 |
| WO | WO 98/51307 A1 | 11/1998 |
| WO | WO 98/51308 A1 | 11/1998 |
| WO | WO 98/55124 A1 | 12/1998 |
| WO | WO 99/00116 A2 | 1/1999 |
| WO | WO 99/11634 A1 | 3/1999 |
| WO | WO 99/18077 A1 | 4/1999 |
| WO | WO 99/29667 A1 | 6/1999 |
| WO | WO 00/13671 * | 3/2000 |
| WO | WO 00/17184 A1 | 3/2000 |
| WO | WO 00/23075 A1 | 4/2000 |
| WO | WO 00/35865 A2 | 6/2000 |
| WO | WO 00/44362 A2 | 8/2000 |

(56) References Cited

FOREIGN PATENT DOCUMENTS

| | | |
|---|---|---|
| WO | WO 00/55168 A1 | 9/2000 |
| WO | WO 00/64888 A1 | 11/2000 |
| WO | WO 01/00554 A2 | 1/2001 |
| WO | WO 01/60775 A1 | 8/2001 |
| WO | WO 01/82916 A2 | 11/2001 |
| WO | WO 01/83456 A1 | 11/2001 |
| WO | WO 01/90051 A1 | 11/2001 |
| WO | WO 02/32377 A2 | 4/2002 |
| WO | WO 02/44189 A1 | 6/2002 |
| WO | WO 02/074307 A1 | 9/2002 |
| WO | WO 02/087556 A2 | 11/2002 |
| WO | WO 02/096426 A1 | 12/2002 |
| WO | WO 03/007959 A1 | 1/2003 |
| WO | WO 03/016292 A1 | 2/2003 |
| WO | WO 03/018008 A1 | 3/2003 |
| WO | WO 03/040256 A2 | 5/2003 |
| WO | WO 03/040257 A1 | 5/2003 |
| WO | WO 03/070236 A2 | 8/2003 |
| WO | WO 03/099274 A1 | 12/2003 |
| WO | WO 03/106435 A1 | 12/2003 |
| WO | WO 2004/017920 A2 | 3/2004 |
| WO | WO 2004/019933 A1 | 3/2004 |
| WO | WO 2004/032846 A2 | 4/2004 |
| WO | WO 2004//037176 A2 | 5/2004 |
| WO | WO 2004/039795 A2 | 5/2004 |
| WO | WO 2004/047755 A2 | 6/2004 |
| WO | WO 2004/056355 A1 | 7/2004 |
| WO | WO 2004/058717 A1 | 7/2004 |
| WO | WO 2004/065392 A1 | 8/2004 |
| WO | WO 2004/072042 A2 | 8/2004 |
| WO | WO 2004/092196 A2 | 10/2004 |
| WO | WO 2004/094452 A2 | 11/2004 |
| WO | WO 2004/108139 A2 | 12/2004 |
| WO | WO 2004/112710 A2 | 12/2004 |
| WO | WO 2005/034960 A1 | 4/2005 |
| WO | WO 2005/042712 A2 | 5/2005 |
| WO | WO 2005/065183 A2 | 7/2005 |
| WO | WO 2005/066162 A1 | 7/2005 |
| WO | WO 2005/075431 A1 | 8/2005 |
| WO | WO 2005/115993 A1 | 12/2005 |
| WO | WO 2006/012577 A2 | 2/2006 |
| WO | WO 2006/071095 A1 | 7/2006 |
| WO | WO 2006/105081 A2 | 10/2006 |
| WO | WO 2007/071055 A1 | 6/2007 |
| WO | WO 2008/092231 A1 | 8/2008 |
| WO | WO 2008092231 A1 * | 8/2008 |
| WO | WO 2008/152471 A1 | 12/2008 |
| WO | WO 2010/015520 A1 | 2/2010 |
| WO | WO 2010/100178 A1 | 9/2010 |
| WO | WO 2010/127099 A2 | 11/2010 |
| WO | WO 2015/025226 A2 | 2/2015 |
| WO | WO 2015/025228 A2 | 2/2015 |

OTHER PUBLICATIONS

Mills, Title: Pharmaceutical excipients—An Overview; pp. 1,3 10 and 13; Jun. 21, 2010.*
Product information downloaded from http://www.signetchem.com/downloads/datasheets/Fmc-biopolymer/Avicel-Ph-301-Specifications.pdf on May 13, 2015.*
Rutesh, H. D.; title: Overview of pharmeceutical excipients used in tablets and capsules; Drug topics, published Oct. 24, 2008.*
Abdel-Jalil et al., "Synthesis and Antitumor Activity of 2-Aryl-7-fluoro-6-(4-methyl-1-piperazinyl)-4(3H)-quinazolinones" Heterocycles 65(9):2061-2070 (2005).
Abdul-Rahman et al., "Dinuclear molybdenum complexes derived from diphenols: electrochemical interactions and reduced species" Polyhedron 16(24):4353-4362 (1997).
Acton et al., "Identification of Scavenger Receptor SR-BI as a High Density Lipoprotein Receptor" Science 271:518-520 (1996).
Asztalos, "High-Density Lipoprotein Metabolism and Progression of Atherosclerosis: New Insights from the HDL Atherosclerosis Treatment Study" Curr. Opin. Cardiol. 19:385-391 (2004).
Baba et al., "Continuous intake of polyphenolic compounds containing cocoa powder reduces LDL oxidative susceptibility and has beneficial effects on plasma HDL-cholesterol concentrations in humans" Am. J. Clin. Nutr. 85:709-717 (2007).
Badimon et al., "Role of High Density Lipoproteins in the Regression of Atherosclerosis" Circulation 86(Suppl. III):86-94 (1992).
Barrans et al., "Pre-β HDL: Structure and Metabolism" Biochim. Biophys. Acta 1300:73-85 (1996).
Barter et al., "Antiinflammatory Properties of HDL" Circ. Res. 95:764-772 (2004).
Barter et al., "High Density Lipoproteins and Coronary Heart Disease" Atherosclerosis 121:1-12 (1996).
Bayly et al., "Electronic and magnetic metal-metal interactions in dinuclear oxomolybdenum(V) complexes across bis-phenolate bridging ligands with different spacers between the phenolate termini: ligand-centered vs. metal-centered redox activity" J. Chem. Soc., Dalton Transactions 9:1401-1414 (2001).
Bertele et al., "Platelet Thromboxane Synthetase Inhibitors with Low Doses of Aspirin: Possible Resolution of the 'Aspirin Dilemma'" Science 220:517-519 (1983).
Beugelmans et al., "One-pot Synthesis of 1-Oxo-1,2-Dihydroisoquinolines (Isocarbostyrils) Via $S_{RN}1$ (Ar) Reactions" Synthesis 9:729-731 (1981).
Bhilare et al., "Ionic-Liquid-Influenced Expeditious and Stereoselective Synthesis of Olefins" Synthetic Communications 37(18):3111-3117 (2007).
Bisagni et al., "A Convenient Way to Dibenzo[c,h]-1,5-Naphthyridines (11-Aza-Benzo[c]phenanthridines)" Tetrahedron 52:10427-10440 (1996).
Bisgaier et al., "A Novel Compound that Elevates High Density Lipoprotein and Activates the Peroxisome Proliferator Activated Receptor" J. Lipid Res. 39:17-30 (1998).
Boyce et al., "The Acylation and Alkylation of o-Tolunitrile. A New Route to 3-Substituted Isocarbostyrils" J. Org. Chem. 31:3807-3809 (1966).
Bradsher et al., "A New Isoquinoline Synthesis Via ORTHO-Substituted Benzylamines" Tetrahedron Lett. 31:3149-3150 (1972).
Bradsher et al., "α-Acyl-o-Tolunitriles as Intermediates in the Preparation of 3-Substituted Isoquinolines and 1-Amino-2-benzopyrylium Derivatives" J. Org. Chem. 43:3817-3820 (1978).
Buhle et al., "Trivalent Carbon. II. Unsymmetrical Hexaaryldimethylperoxides" J. Am. Chem. Soc. 65:584-586 (1943).
CAPLUS Accession No. 1991:449453, Liu et al. "Synthesis of 2-aryl-9-bromo-4-oxo-4H-pyrano[3,2-c] quinolines" [online]. Retrieved from STN on Jan. 31, 2011. Also published in: Youji Huaxue 11(2):191-195 (1991).
CAPLUS Accession No. 2003:554477, Qin et al., "Synthesis and fungicidal activity of novel diazaflavanones" [online]. Retrieved from STN on Jan. 31, 2011. Also published in: Nongyaoxue Xuebao 4(4):28-32 (2002).
CAPLUS Accession No. 2004:11346, Hu et al., "Synthesis and fungicidal activity of flavanone derivatives containing isopentenyl group" [online]. Retrieved from STN on Jan. 31, 2011. Also published in: Yingyong Huaxue 20(12):1161-1165 (2003).
CAPLUS Accession No. 2005:46491, Qin et al., "Synthesis and fungicidal activity of 5,7-dihydroxyldiazinflavanones" [online]. Retrieved from STN on Jan. 31, 2011. Also published in: Huazhong Shifan Daxue Xuebao Zirankexueban38(3):323-325 (2004).
Chakrabarty et al., "Induction of apoptosis in human cancer cell lines by diospyrin, a plant-derived bisnaphthoquinonoid, and its synthetic derivatives" Cancer Letters 188(1-2):85-93 (2002).
Chartier et al., "Synthèse de diazaflavones" Bull. Soc. Chim. Fr. 11-12(Pt. 2):1916-1918 (1976). English abstract on p. 1916.
Cherubini et al., "Role of Antioxidants in Atherosclerosis: Epidemiological and Clinical Update" Curr. Pharm. Des. 11:2017-2032 (2005).
Cho et al., "Molecular Modeling of 3-Arylisoquinoline Antitumor Agents Active Against A-549. A Comparative Molecular Field Analysis Study" Bioorg. Med. Chem. 10:2953-2961 (2002).
Cho et al., "Synthesis and Antitumor Activity of 3-Arylisoquinoline Derivatives" Arch. Pharm. Res. 20:264-268 (1997).

(56) References Cited

OTHER PUBLICATIONS

Cho et al., "Synthesis and Biological Evaluation of 3-Arylisoquinolines as Antitumor Agents" *Bioorg. Med. Chem. Lett.* 8:41-46 (1998).

Cho et al., "Synthesis and Comparative Molecular Field Analysis (CoMFA) of Antitumor 3-Arylisoquinoline Derivatives" *Bioorg. Med. Chem.* 6(12):2449-2458 (1998).

Chyu et al., "Differential Effects of Green Tea-Derived Catechin on Developing Versus Established Atherosclerosis in Apolipoprotein E-Null Mice" *Circulation* 109:2448-2453 (2004).

Clarkson et al., "Inhibition of Postmenopausal Atherosclerosis Progression: A Comparison of the Effects of Conjugated Equine Estrogens and Soy Phytoestrogens" *J. Clin. Endocrinol. Metab.* 86(1):41-47 (2001).

Clauson-Kaas et al., "Reactions of 3,4-dihydor-2H-pyrrido[3,2-b]-1,4-oxazines" *Acta Chemica Scandinavica* 25(8):3135-3143 (1971). Retrieved from STN, file HCAPLUS, Accession No. 1972:34186 (Abstract).

Connolly et al., "Synthesis of quinazolinones and quinazolines" *Tetrahedron* 61(43):10153-10202 (2005).

Cooper et al., "Wine polyphenols and promotion of cardiac health" *Nutr. Res. Rev.* 17:111-129 (2004).

Cramer et al., "New Syntheses of Aryl Fluorides and Aryl Fluorosulfonates from Oxyflourides of Sulfur" *J. Org. Chem.* 26:4164-4165 (1961).

Dai et al., "Synthesis of 3,4-Disubstituted Isoquinolines via Palladium-Catalyzed Cross-Coupling of 2-(1-alkynyl)benzaldimines and Organic Halides" *J. Org. Chem.* 68:920-928 (2003).

Dai et al., "Synthesis of 3-Substituted 4-Aroylisoquinolines via Pd-Catalyzed Carbonylative Cyclization of 2-(1-Alkynyl)benzaldimines" *J. Org. Chem.* 67:7042-7047 (2002).

Dansky et al., "High-Density Lipoprotein and Plaque Regression. The Good Cholesterol Gets Even Better" *Circulation* 100:1762-1763 (1999).

Decossin et al., "Subclasses of LpA-I in Coronary Artery Disease: Distribution and Cholesterol Efflux Ability" *Eur. J. Clin. Invest.* 27:299-307 (1997).

Devitt et al., "Synthesis of Heterocyclic-Substituted Chromones and Chalcones" *J. Org. Chem.* 26:4941-4944 (1961).

Edwards et al., "Inhibition of myeloperoxidase release from rat polymorphonuclear leukocytes by a series of azachalcone derivatives" *J. Med. Chem.* 37(25):4357-4362 (1994).

Eiden et al., "1,2-Bisbenzopyranyl-ethene" *Archiv. der Pharmazie* 313(2):120-128 (1980) (German; English abstract on p. 120).

Esterbauer et al., "Continuous Monitoring of In Vitro Oxidation of Human Low Density Lipoprotein" *Free Rad. Res. Comms.* 6:67-75 (1989).

Ferreira et al., "Diversity of Structure and Function in Oligomeric Flavanoids" *Tetrahedron* 48:1743-1803 (1992).

Fielding et al., "Molecular Physiology of Reverse Cholesterol Transport" *J. Lipid Res.* 36:211-228 (1995).

Fieser, L.F., "The potentials of some unstable oxidation-reduction systems" *J. Am. Chem. Soc.* 52:4915-4940 (1930).

Fisher Center for Alzheimer's Research Foundation, "Alzheimer's Disease: 'Good' Cholesterol May Help Keep Alzheimer's at Bay" The Ninth International Conference on Alzheimer's Disease and Related Disorders, Philadelphia, PA, Jul. 22, 2004. Retrieved from the Internet: http://www.alzinfo.org/newsarticle/templates/archivenewstemplate.asp?articleid=156&zoneid=7 on Jul. 28, 2010 (3 pages).

Flammang et al., "2,3-Benzodiazepines: 2-Aminoisoquinolinones From Ring Contraction of 1-oxo-2,3-Benzodiazepines" *C R Acad. Sci. Paris, Series C* 290:361-363 (1980) (French; English abstract on p. 361).

Fokialakis et al., "A New Class of Phytoestrogens: Evaluation of the Estrogenic Activity of Deoxybenzoins" *Chem. Biol.* 11:397-406 (2004).

Gaziano et al., "Relation Between Systemic Hypertension and Blood Lipids on the Risk of Myocardial Infarction" *Am. J. Cardiol.* 84(7):768-773 (1999).

Gerritsen et al., "Flavenoids inhibit cytokine-induced endothelial cell adhesion protein gene expression" *Am. J. Pathol.* 147(2):278-292 (1995).

Gidez et al., "Separation and Quantitation of Subclasses of Human Plasma High Density Lipoproteins by a Simple Precipitation Procedure" *J. Lipid Res.* 23:1206-1223 (1982).

Gordon et al., "High Density Lipoprotein as a Protective Factor Against Coronary Heart Disease" *Am. J. Med.* 62(5):707-714 (1977).

Grundy et al., "Definition of Metabolic Syndrome. Report of the National Heart, Lung and Blood Institute/American Heart Association Conference on Scientific Issues Related to Definition" *Circulation* 109:433-438 (2004).

Gugler et al., "Disposition of Quercetin in Man after Single Oral and Intravenous Doses" *Eur. J. Clin. Pharmacol.* 9:229-234 (1975).

Guillory, J.K., "Generation of Polymorphs, Hydrates, Solvates, and Amorphous Solids" Brittain, Harry G. (ed.) *Polymorphism in Pharmaceutical Solids*, vol. 95. Marcel Dekker, Inc., New York; pp. 202-208 (1999).

Hakamata et al., "Differential effects of an acyl-coenzyme A: cholesterol acyltransferase inhibitor on HDL-induced cholesterol efflux from rat macrophage foam cells" *FEBS Letters* 363:29-32 (1995).

Haneke, "trans-Resveratrol, [501-36-0], Review of Toxicological Literature" Nat. Inst. Environ. Health Sciences Contract No. N01-ES-65402 (Mar. 2002).

Hazra et al., "New diospyrin derivatives with improved tumour inhibitory activity towards Ehrlich ascites carcinoma" *Medical Science Research* 22(5):351-353 (1994).

Hazra et al., "Synthesis of an antitumor derivative of diospyrin" *IRCS Medical Science* 14(1):35-36 (1986).

Heeg et al., "Plasma Levels of Probucol in Man after Single and Repeated Oral Doses" *La Nouvelle Presse Medicale* 9:2990-2994 (1980) (English abstract on p. 2990).

Hemingway et al., "A gas-liquid chromatographic examination of stilbene derivatives" *J. Chromatog.* 50(3):391-399 (1970).

Hertog et al., "Dietary Antioxidant Flavonoids and Risk of Coronary Heart Disease: the Zutphen Elderly Study" *Lancet* 342:1007-1011 (1993).

Hidaka et al., "Affinity Purification of the Hepatic High-Density Lipoprotein Receptor Identifies Two Acidic Glycoproteins and Enables Further Characterization of Their Binding Properties" *Biochem. J.* 284:161-167 (1992).

Hirano et al., "Genetic Cholesteryl Ester Transfer Protein Deficiency Is Extremely Frequent in the Omagari Area of Japan. Marked Hyperalphalipoproteinemia Caused by CETP Gene Mutation is not Associated With Longevity" *Arterioscler Thromb. Vasc. Biol.* 17:1053-1059 (1997).

Hisano et al., "Studies on Organosulfur Compounds. XII. Syntheses and Pharmacological Activities of 2-Heterocyclic Substituted 4(3H)-Quinazolinones" *Chem. Pharm. Bull.* 23(9):1910-1916 (1975).

Huang et al., "Synthesis of Isoquinolines by Palladium-Catalyzed Cyclization, Followed by a Heck Reaction" *Tetrahedron Lett.* 43:3557-3560 (2002).

Hwang et al., "Syntergistic inhibition of LDL oxidation by phytoestrogens and ascorbic acid" *Free Radical Biology and Medicine* 29(1):79-89 (Jul. 1, 2000).

International Search Report and Written Opinion issued in International Application No. PCT/CA2004/001818; Date of Mailing: Feb. 28, 2005.

International Search Report and Written Opinion issued in International Application No. PCT/CA2007/000146; Date of Mailing: Oct. 29, 2007.

International Search Report and Written Opinion issued in International Application No. PCT/IB2010/000159; Date of Mailing: Aug. 5, 2010.

International Search Report and Written Opinion issued in International Application No. PCT/IB2010/000826; Date of Mailing: Oct. 12, 2010.

International Search Report and Written Opinion issued in International Application No. PCT/US2010/031870; Date of Mailing: Jul. 1, 2010.

(56) References Cited

OTHER PUBLICATIONS

International Search Report and Written Opinion issued in International Application No. PCT/IB2012/002721; Date of Mailing: Mar. 14, 2013.
International Search Report and Written Opinion issued in International Application No. PCT/US2005/037719; Date of Mailing: Mar. 9, 2007.
International Search Report and Written Opinion issued in International Application No. PCT/US2005/038048; Date of Mailing: Mar. 7, 2007.
International Search Report and Written Opinion issued in International Application No. PCT/US2006/029827; Date of Mailing: Apr. 16, 2007.
International Search Report and Written Opinion issued in International Application No. PCT/US2009/048457; Date of Mailing: Oct. 16, 2009.
Ishibashi et al., "Hypercholesterolemia in Low Density Lipoprotein Receptor Knockout Mice and its Reversal by Adenovirus-Mediated Gene Delivery" *J. Clin. Invest.* 92:883-893 (1993).
Ishibashi et al., "Massive Xanthomatosis and Atherosclerosis in Cholesterol-Fed Low Density Lipoprotein Receptor-Negative Mice" *J. Clin. Invest.* 93:1885-1893 (1994).
Japanese Office Action issued in Japanese Patent Application No. 2008-524272, mailed Jul. 24, 2012, with English translation.
Jayatilake et al., "Kinase Inhibitors From *Polygonum cuspidatum*" *J. Nat. Prod.* 56:1805-1810 (1993).
Jensen et al., "Serum Lipids and Anthropometric Factors Related to the Prevalence of Intermittent Claudication" *Eur. J. Vasc. Endovasc. Surg.* 30:582-587 (2005).
Jeong et al., "Hypocholesterolemic activity of hesperetin derivatives" *Bioorg. Med. Chem. Lett.* 13:2663-2665 (2003).
Jin et al., "Antiplatelet and antithrombotic activities of CP201, a newly synthesized 1,4-naphthoquinone derivative" *Vasc. Pharmacol.* 41(1):35-41 (2004).
Kalusa et al., "An efficient synthesis of 2,3-diaryl (3H)-quinazolin-4-ones via imidoyl chlorides" *Tetrahedron Letters* 49(41):5840-5842 (2008).
Kawamatsu et al., "2-Amino-4-Phenylthiazole Derivatives as Anti-Atherogenic Agents" *Eur. J. Med. Chem.—Chimica Therapeutica* 16(4):355-362 (1981).
Kilbourne et al., "Involvement of Early Growth Response Factor Egr-1 in Apolipoprotein Al Gene Transcription" *J. Biol. Chem.* 270:7004-7010 (1995).
Kim et al., "Hypothetical Drug Binding Receptor Site Analysis Using CoMFA Method for 3-Arylisoquinolines Active Against SK-OV-3 Tumor Cell Line" *Yakhak Hoechi* 46(4):219-225 (2002) (English abstract on p. 219), English abstract only.
Koudinov et al., "Alzheimer's amyloid beta and lipid metabolism: a missing link?" *FASEB J.* 12:1097-1099 (1998).
Kublak et al., "The preparation of the aza-spirobicyclic system of discorhabdin C via an intramolecular phenolate alkylation" *Tetrahedron Lett.* 31(27):3845-3848 (1990).
Kulkarni et al.,"Quantification of $HDL_2$ and $HDL_3$ Cholesterol by the Vertical Auto Profile-II (VAP-II) Methodology" *J. Lipid Res.* 38:2353-2364 (1997).
Kurata et al., "A Candidate High Density Lipoprotein (HDL) Receptor, $HB_2$, with Possible Multiple Functions Shows Sequence Homology with Adhesion Molecules" *J. Atheroscler. Thromb.* 4:112-117 (1998).
Kurowska et al., "Essential Amino Acids in Relation to Hypercholesterolemia Induced in Rabbits by Dietary Casein" *J. Nutr.* 120:831-836 (1990).
Kuzuya et al., "Probucol Prevents Oxidative Injury to Endothelial Cells" *J. Lipid Res.* 32:197-204 (1991).
Laarhoven et al., "Syntheses, infrared spectra and molecular refractions of some sterically hindered p,p'-dimethoxystilbenes. Influence of non-planarity in styrene and stilbene derivatives IV" *Recueil des Travaux Chimiques des Pays-Bas* 80:775-791 (1961).

Lagrost et al., "Opposite Effects of Cholesteryl Ester Transfer Protein and Phospholipid Transfer Protein on the Size Distribution of Plasma High Density Lipoproteins" *J. Biol. Chem.* 271:19058-19065 (1996).
Lamon-Fava, "Genistein activates apolipoprotein A-I gene expression in the human hepatoma cell line Hep G2" *J. Nutrition* 130:2489-2492 (2000).
Landshulz et al., "Regulation of Scavenger Receptor, Class B, Type I, a High Density Lipoprotein Receptor, in Liver and Steroidogenic Tissues of the Rat" *J. Clin. Invest.* 98:984-995 (1996).
Letan, "The Relation of Structure to Antioxidant Activity of Quercetin and some of Its Derivatives. I. Primary Activity" *J. Food Sci.* 13(4):518-523 (1966).
Lin et al., "Chemoprevention of Cancer and Cardiovascular Disease by Resveratrol" *Proc. Natl. Sci. Counc. ROC (B)* 23:99-106 (1999).
Lin et al., "Potential bioreductive alkylating agents. 7. Antitumor effects of phenyl-substituted 2-chloromethyl-3-phenyl-1,4-naphthoquinones" *J. Med. Chem.* 19(11):1336-1338 (1976).
Lin et al., "Solvent Effects on Aza-Anionic Cycloaromatization of 2-(2-Substituted-Ethynyl)Benzonitriles" *J. Chinese Chem. Soc.* 48:211-214 (2001).
Lin et al., "The Role of Absorption, Distribution, Metabolism, Excretion and Toxicity in Drug Recovery" *Curr. Top. Med. Chem.* 3:1125-1154 (2003).
Linnell et al. "Isomers of stilbestrol. II." *Q. J. Pharm. Pharmacol.* 15:384-388 (1942).
Lopez et al., "The Synthesis of Substituted 2-Aryl-4(3H)-quinazolinones using $NaHSO_3$/DMA. Steric Effect Upon the Cyclisation-Dehydrogenation Step" *J. Chem. Research (S)*, pp. 258-259 (2000).
Maher et al., "Lipoprotein (a) and coronary heart disease" *Curr. Opin. Lipidol.* 6:229-235 (1995).
Mahto et al., "Synthesis of 3-Aryl-7-Hydroxy Isochromenes" *Asian J. Chem.* 11(2):431-435 (1999).
Manach et al., "Polyphenols and prevention of cardiovascular diseases" *Curr. Opin. Lipidol.* 16:77-84 (2005).
Marks, F., "Epidermal Growth Control Mechanisms, Hyperplasia, and Tumor Promotion in the Skin" *Cancer Res.* 36:2636-2343 (1976).
Martin et al., "Modified Flavinoids as Strong Photoprotecting UV-Absorbers and Antioxidants" *Strategies for Safe Food*. Eklund, T. et al. (Eds.), vol. 1, pp. 288-291 (2003).
McKee et al., "Some Basically Substituted Quinazolines" *J. Am. Chem. Soc.* 68(10):1902-1903 (1946).
Meckes et al., "The effects of chrysin and pinostrobin, 2 flavonoids isolated from *Teloxys graveolens* leaves, on isolated guinea-pig ileum" *Phytomedicine* 5(6):459-463 (1998).
Melani et al., "Tricyclic heterocyclic systems: pyrazolo[5',4':4,5]- and pyrazolo-[3',4':4,5]pyrano[2,3-B]pyridine derivatives" *J. Heterocyclic Chem.* 25:1367-1371 (1988).
Middleton et al., "Quercetin inhibits lipopolysaccharide-induced expression of endothelial cell intracellular adhesion molecule-1" *Int. Arch. Allergy Immunol.* 107:435-436 (1995).
Moffett, "Azacoumarins" *J. Org. Chem.* 35(11):3596-3600 (1970).
Mondal et al., "Two-Stage Chemical Oncogenesis in Cultures of C3H/10T1/2 Cells" *Cancer Res.* 36:2254-2260 (1976).
Nicholls et al., "Efficacy and Safety of a Novel Oral Inducer of Apolipoprotein A-I Synthesis in Statin-Treated Patients with Stable Coronary Artery Disease" *J. Am. Coll. Cardiol.* 57(9):1111-1119 (2011).
Nigam et al., "Synthesis and Pharmacological Screening of Some New 2-(Phenyl/Chloromethyl)-3-[4 (N, N-Disubstituted Aminocarbonyl) Phenyl]-8-Substituted-4 (3H)-Quinazolones" *Indian Drugs* 27(4):238-243 (1990).
Nissen et al., "Effect of Recombinant ApoA-I Milano on Coronary Atherosclerosis in Patients with Acute Coronary Syndroms: A Randomized Controlled Trial" *JAMA* 290(17):2292-2300 (2003).
Nourooz-Zadeh, "Ferrous Ion Oxidation in Presence of Xylenol Orange for Detection of Lipid Hydroperoxides in Plasma" *Methods Enzymol.* 300:58-62 (1999).

(56) References Cited

OTHER PUBLICATIONS

Ohtomo et al., "Comparative activities of daidzein metabolites, equol and O-desmethylangolensin, on bone mineral density and lipid metabolism in ovariectomixed mice and in osteoclast cell cultures" *Eur. J. Nutr.* 47(5):273-279 (2008).
Ordovas, J.M., "Gene-diet interaction and plasma lipid responses to dietary intervention" *Biochem. Soc. Trans.* 30(2):68-73 (2002).
Parra et al., "A Case-Control Study of Lipoprotein Particles in Two Populations at Contrasting Risk for Coronary Heart Disease" *Arterioscler. Thromb.* 12:701-707 (1992).
Patani et al., "Bioisosterism: A Rational Approach in Drug Design" *Chem. Rev.* 96(8):3147-3176 (1996).
Pearson et al., "The ortho Bromination of Phenols" *J. Org. Chem.* 32:2358-2360 (1967).
Pettit et al., "Antineoplastic Agents. 465. Structural Modification of Resveratrol: Sodium Resverastatin Phosphate" *J. Med. Chem.* 45:2534-2542 (2002).
Plump et al., "Human apolipoprotein A-I gene expression increases high density lipoprotein and suppresses atherosclerosis in the apolipoprotein E-deficient mouse" *Proc. Natl. Acad. Sci. USA* 91:9607-9611 (1994).
Quinones et al., "The egr-1 gene is induced by DNA-damaging agents and non-genotoxic drugs in both normal and neoplastic human cells" *Life Sciences* 72(26):2975-2992 (2003).
Ragione et al., "Antioxidants induce different phenotypes by a distinct modulation of signal transduction" *FEBS Letters* 523:289-294 (2002).
Ragione et al., "p21$^{CIP}$1 Gene Expression is Modulated by Egr1: A Novel Regulatory Mechanism Involved in the Resveratrol Antiproliferative Effect" *J. Biol. Chem.* 278:23360-23368 (2003).
Rajakumar et al., "TiCl$_4$, Dioxane—A facile and efficient system for de-O-benzylation, de-O-allylation, and de-O-xylylation of phenolic ethers" *Synthetic Communications* 33(22):3891-3896 (2003).
Raun et al., "Apolipoprotein A-I possesses an anti-obesity effect associated with increase of energy expenditure and upregulation of UCP1 in brown fat" *J. Cell. Mol. Med.* (2010). "Postprint"; 10.1111/j.1582.4934.2010.01045.x.
Rice-Evans, "Flavonoids and Isoflavones: Absorption, Metabolism, and Bioactivity" *Free Radical Biol. Med.* 36:827-828 (2004).
Richtzenhain, H. "Estrogenic stilbene and diphenylethane derivatives. II." *Chemische Berichte* 82:405-407 (1949) (German).
Rigotti et al., "Regulation by Adrenocorticotropic Hormone of the in Vivo Expression of Scavenger Receptor Class B Type I (SR-BI), a High Density Lipoprotein Receptor, in Steroidogenic Cells of the Murine Adrenal Gland" *J. Biol. Chem.* 271:33545-33549 (1996).
Rimando et al., "Pterostilbene, a New Agonist for the Peroxisome Proliferator-Activated Receptor α-Isoform, Lowers Plasma Lipoproteins and Cholesterol in Hypocholesterolemic Hamsters" *Journal of Agricultural and Food Chemistry* 53(9):3403-3407 (2005).
Rodriguez et al., "Novel Effects of the Acyl-Coenzyme A: Cholesterol Acyltransferase Inhibitor 58-035 on Foam Cell Development in Primary Human Monocyte-Derived Macrophages" *Arterioscler. Thromb. Vasc. Biol.* 19:2199-2206 (1999).
Rose et al., "Oxygen Heterocycles. XIII. From 3-Arylisocoumarins to 3-Arylisoquinolines and 4-Aryl-5H-2,3-Benzodiazepines" *J. Chem. Soc. [Section] C: Organic* 17:2205-2208 (1968).
Rubin et al., "Expression of Human Apolipoprotein A-I in Transgenic Mice Results in Reduced Plasma Levels of Murine Apolipoprotein A-I and the Appearance of Two New High Density Lipoprotein Size Subclasses" *Proc. Natl. Acad. Sci. USA* 88:434-438 (1991).
Rubin et al., "Inhibition of Early Atherogenesis in Transgenic Mice by Human Apolipoprotein AI" *Nature* 353:265-267 (1991).
Rubins et al., "Reduction in Stroke with Gemfibrozil in Men with Coronary Heart Disease and Low HDL Cholesterol. The Veterens Affairs HDL Intervention Trial (VA-HIT)" *Circulation* 103:2828-2833 (2001).
Sarkhel et al., "3-Arylisocoumarin: Synthesis of 3-(4-methoxyphenyl)-isocoumarin" *J. Indian Chem. Soc.* 53:915-916 (1976).

Schiess et al., "Thermolytic Ring Opening of Acyloxybenzocyclobutenes: An Efficient Route to 3-Substituted Isoquinolines" *Tetrahedron Lett.* 26:3959-3962 (1985).
Schmutz et al., "Synthese von basisch substituierten Chromonen" *Helv. Chim. Acta* 36:620-626 (1953) (German).
Schork, N.J., "Genetics of Complex Disease. Approaches, Problems, and Solutions" *Am. J. Respir. Crit. Care Med.* 156(4):S103-109 (Oct. 1997).
Schultz et al., "Role of stilbenes in the natural durability of wood: fungicidal structure-activity relationships" *Phytochemistry* 29(5):1501-1507 (1990).
Shah et al., "Effects of Recombinant Apolipoprotein A-I$_{Milano}$ on Aortic Atherosclerosis in Apolipoprotein E-Deficient Mice" *Circulation* 97(8):780-785 (1998).
Shapiro et al., "Micro Assay for 3-Hydroxy-3-Methylglutaryl-CoA Reductase in Rat Liver and L-Cell Fibroblasts" *Biochim. Biophys. Acta* 370:369-377 (1974).
Sharrett et al., "Associations of Lipoprotein Cholesterols, Apolipoproteins A-I and B, and Triglycerides with Carotid Atherosclerosis and Coronary Heart Disease. The Atherosclerosis Risk in Communities (ARIC) Study" *Arterioscler. Thromb.* 14:1098-1104 (1994).
Sieber, R.H., "Reactions of chloroacetaldehyde with aromatic hydrocarbons, phenols, and phenol ethers" *Justus Liebigs Annalen der Chemie* 730:31-46 (1969) (German; English abstract on p. 31).
Sliwa et al., "Tautomerie entre structures α-aleoxy-enaminocetone et β-ceto iminoether presentee par les piperidines resultant de la semihydrogenation d'alcoxy-2-acyl-3 pyridines" *J. Heterocyclic Chem.* 16:939-944 (1979) (French; English summary on p. 944).
Slowing et al., "Anti-Inflammatory Activity of Leaf Extracts of *Eugenia jambos* in Rats" *J. Ethnopharmacol.* 43:9-11 (1994).
Smyth et al., "Non-amine based analogues of lavendustin A as protein-tyrosine kinase inhibitors" *J. Med. Chem.* 36(20):3010-3014 (1993).
Sun et al., "In Vitro Testing of Drug Absorption for Drug 'Developability' Assessment: Forming an Interface Between in Vitro Preclinical Data and Clinical Outcome" *Curr. Opin. Drug Discov. Devel.* 7:75-85 (2004).
Suryadevara et al., "Association of Abnormal Serum Lipids in Elderly Persons with Artherosclerotic Vascular Disease and Demetia, Artheroslerotic Vascular Disease Without Demetia, Demetia Without Artherosclerotic Vascular Disease, and No Dementia or Artherosclerotic Vascular Disease" *J. Gerontol. Med. Sci.* 58A(9):859-861 (2003).
Tait et al., "Synthesis and Free Radical Scavenging Activity of 4-(2H-1,2,4-Benzothiadiazine-1,1-dioxide-3-yl)-2,6-bis(1,1-dimethylethyl)phenols" *Tetrahedron* 52(38):12587-12596 (1996).
Talbert, "Current Recommendations for the Treatment of Dyslipidemia" *Pharm. Ther.* 29:104 (2004).
Tanne et al., "High-Density Lipoprotein Cholesterol and Risk of Ischemic Stroke Mortality" *Stroke* 28:83-87 (1997).
Tardif et al., "Probucol and Multivitamins in the Prevention of Restenosis After Coronary Angioplasty" *N. Engl. J. Med.* 337:365-367 (1997).
Theriault et al., "Modulation of hepatic lipoprotein synthesis and secretion by taxifolin, a plant flavonoid," *J. Lipid Res.* 41:1969-1979 (2000).
Toth et al., "Therapeutic Interventions Targeted at the Augmentation of Reserve Cholesterol Transport" *Curr. Opin. Cardiol.* 19:374-379 (2004).
Tovar et al., "Pyrylium Salts via Electrophilic Cyclization: Applications for Novel 3-Arylisoquinoline Syntheses" *J. Org. Chem.* 64:6499-6504 (1999).
Tudan, "Selective Inhibition of Protein Kinase C, Mitogen-Activated Protein Kinase, and Neutrophil Activation in Response to Calcium Pyrophosphate Dihydrate Crystals, Formyl-Methionyl-Leucyl-Phenylalanine, and Phorbol Ester by O-(Chloroacetyl-carbamoyl) Fumagillol (AGM-01470; TNP-470)" *Biochem. Pharmacol.* 58:1869-1880 (1999).
Utermann, "The Mysteries of Lipoprotein(a)" *Science* 246:904-910 (1989).

(56) References Cited

OTHER PUBLICATIONS

Van Der Goot et al., "The Growth-Inhibitory Action of Some 1-Aminoisoquinolines and Related Compounds on Mycoplasma Gallisepticum" *Eur. J. Med. Chem.—Chimica Thereapeutica* 10:603-606 (1975).
Varin et al., "Enzymatic Assay for Flavonoid Sulfotransferase" *Anal. Biochem.* 161:176-180 (1987).
Vippagunta et al., "Crystalline solids" *Adv. Drug Delivery Rev.* 48:3-26 (2001).
Walle, "Absorption and Metabolism of Flavonoids" *Free Radical Biol. Med.* 36(7):829-837 (2004).
Webster Ninth New Collegiate Dictionary, Definition of 'Prevent', 1 page (2000).
Wei et al., "Total Cholesterol and High Density Lipoprotein Cholesterol as Important Predictors of Erectile Dysfunction" *Am. J. Epidemiol.* 140(10):930-937 (1994).
Welsh et al., "Dyslipidemia in Diabetic Patients" *Prospectives in Cardiology,* Aug. 2002, pp. 40-48.
Wölle et al., "Selective inhibition of tumor necrosis factor-induced vascular cell adhesion molecule-1 gene expression by a novel flavonoid. Lack of effect on transcription factor NF-kappa-B" *Arterioscler. Thromb. Vasc. Biol.* 16(12):1501-1508 (1996).
Wurm et al., "1,4-Naphthoquinones, XXVI: Phenyl-1,4-naphthoquinone derivatives with the hydroxylation patterns of bioflavonoids" *Pharmazie* 52(10):739-743 (1997) (German; English abstract on p. 739).
Wurm, "1,4-Naphthoquinones, XXI: 2-(3,5 Di-tert-butyl-4-hydroxyphenyl)-1,4-naphtoquinones as 5-lipozxygenase inhibitors" *Archiv. der Pharmazie* 324(8):491-495 (1991) (German; English abstract on p. 491).
Yamakoshi et al., "Isoflavone aglycone-rich extract without soy protein attenuates atherosclerosis development in cholesterol-fed rabbits" *Journal of Nutrition* 130(8):1887-1893 (2000).
Yardley et al., "In vitro activity of diospyrin and derivatives against *Leishmania donovani, Trypanosoma cruzi* and *Trypanosoma brucei brucei*" *Phytotherapy Research* 10(7):559-562 (1996).
Yoshioka et al., "Semiempirical Investigation of Stilbene-Linked Diradicals and Magnetic Study of Their Bis(N-tert-butylnitroxide) Variants" *J. Org. Chem.* 59(15):4272-4280 (1994).
Office Action in U.S. Appl. No. 11/255,103: Restriction Requirement, mailed Mar. 26, 2008.
Office Action in U.S. Appl. No. 11/255,103, mailed Sep. 24, 2008.
Office Action in U.S. Appl. No. 11/255,103 mailed Aug. 31, 2009.
Office Action in U.S. Appl. No. 11/255,103, mailed Mar. 31, 2010.
Office Action in U.S. Appl. No. 11/255,103, mailed Nov. 10, 2010.
Office Action in U.S. Appl. No. 11/255,103: Notice of Allowance, mailed Jun. 7, 2011.
Office Action in U.S. Appl. No. 11/255,103: Notice of Allowance, mailed Sep. 15, 2011.
Office Action in U.S. Appl. No. 11/670,238: Restriction Requirement, mailed Mar. 31, 2010.
Office Action in U.S. Appl. No. 11/670,238: Restriction Requirement, mailed Jul. 20, 2010.
Office Action in U.S. Appl. No. 11/670,238, mailed Oct. 7, 2010.
Office Action in U.S. Appl. No. 11/670,238, mailed Apr. 19, 2011.
Office Action in U.S. Appl. No. 11/670,238, mailed Jun. 22, 2011.
Office Action in U.S. Appl. No. 11/670,238: Notice of Allowance, mailed Aug. 3, 2011.
Office Action in U.S. Appl. No. 11/670,238: Notice of Allowance, mailed Sep. 16, 2011.
Office Action in U.S. Appl. No. 11/990,162: Restriction Requirement, mailed Jul. 10, 2009.
Office Action in U.S. Appl. No. 11/990,162, mailed Oct. 14, 2009.
Office Action in U.S. Appl. No. 11/990,162, mailed Apr. 1, 2010.
Office Action in U.S. Appl. No. 11/990,162, mailed Dec. 28, 2010.
Office Action in U.S. Appl. No. 11/990,162, mailed Sep. 26, 2011.
Office Action in U.S. Appl. No. 11/990,162, mailed Mar. 19, 2012.
Office Action in U.S. Appl. No. 12/369,296, mailed Nov. 10, 2011.
Office Action in U.S. Appl. No. 12/369,296, mailed Mar. 13, 2012.
Office Action in U.S. Appl. No. 12/369,296: Notice of Allowance, mailed Apr. 12, 2012.
Office Action in U.S. Appl. No. 12/490,877, mailed Sep. 15, 2011.
Office Action in U.S. Appl. No. 12/490,877: Notice of Allowance, mailed Nov. 25, 2011.
Office Action in U.S. Appl. No. 13/243,776, mailed Apr. 11, 2013.
Office Action in U.S. Appl. No. 13/265,060, mailed Apr. 3, 2013.
International Search Report and Written Opinion issued in International Application No. PCT/IB2013/003031; Date of Mailing: May 28, 2014.
Mitchell et al., "Bromination of 4,6-dimethoxyindoles" *Tetrahedron* 68(39):8163-8171 (2012).
Colaizzi and Klink (1969) "pH-Partition Behavior of Tetracyclines" *J. Pharm. Sci.,* 58(10):1184-1189.
Hunziker and Nissen (1926) "Lactose Solubility and Lactose Crystal Formation. I. Lactose Solubility" *J. Dairy Sci.,* 9(6):517-537.
TOKU-E Product Data Sheet, "Oxytetracycline dihydrate" [online], Retrieved from the Internet: http://www.toku-e.com/product/oxytetracycline_dihydrate on Feb. 5, 2015 ( 2 pages).
Van De Waterbeemd et al. (1997) "Glossary of Terms Used in Computational Drug Design" *Pure & Appl. Chem.,* 69(5):1137-1152.
Cabot Corporation, "Untreated Fumed Silica: CAB-O-SIL® M-5" Product Information, PDS-147 (2004) (2 pages).
Extended European Search Report, including Supplementary Search Report and Opinion, issued Jun. 1, 2015, in European Patent Application 12844794.3, filed May 12, 2014, by Resverlogix Corp.
"Gildants" in *Remington. The Science and Practice of Pharmacy.* 21st Edition. David B. Troy (Ed.). Philadelphia, PA: Lippincott Williams & Wilkins, 2006; p. 893.
Kamel et al., "Pharmaceutical significance of cellulose: A review" *eXPRESS Polymer Letters* 2(11):758-778 (2008).
McLure et al., "RVX-208, an Inducer of ApoA-I in Humans, is a BET Bromodomain Antagonist" *PLOS One,* 8(12):e83190 (2013) (12 pages).
Naden, C., "Methaqualone"in *The Facts About the A-Z of Drugs.* Tarrytown, NY: Marshall Cavendish Benchmark, 2008; pp. 92-94.
"RVX 208" R&D Insight Profile in *Drugs* 11(2):207-213 (2011).
Terinte et al., "Overview on native cellulose and microcrystalline cellulose I structure studied by x-ray diffraction (WAXD): Comparison between measurement techniques" *Lenzinger Berichte* 89:118-131 (2011).
Thoorens et al., "Microcrystalline cellulose, a direct compression binder in a quality by design environmen—A review" *Intl. J. Pharmaceut.* 473:64-72 (2014).
Office Action mailed Sep. 20, 2016 in Russian Patent Application No. 2014115427/15(024178), filed Oct. 31, 2012, by Resverlogix Corp., CA: (English translation, 7 pages).
Chueshov et al. (Eds.) *Industrial Technology of Drugs:* Handbook. vol. 1. MTK-Kniga; Publish. NFAU. 2002. (English Abstract only; original in Russian) (1 page).
Rowe, R.C. et al. (Eds.) *Handbook of Pharmaceutical Excipients.* 5th ed. Great Britain: Pharmaceuticals Press and the American Pharmacists Association, 2006 (940 pages).

\* cited by examiner

PHARMACEUTICAL COMPOSITIONS FOR SUBSTITUTED QUINAZOLINONES

This application claims the benefit of U.S. Provisional Application No. 61/554,090, filed Nov. 1, 2011, which is incorporated herein by reference in its entirety.

Epidemiologic data demonstrate an inverse relationship between circulating levels of high density lipoprotein cholesterol (HDL-C) and the incidence of clinically significant atherosclerosis. Each 1 mg/dl increment in the HDL-C serum level is associated with a 2-3% decrement in cardiovascular risk; a 1% reduction in LDL-C reduces coronary heart disease (CHD) risk by 2% (Gordon et al. (1997) *Am. J. Med.* 62, 707-714). Experimental evidence further supports the protective effect of HDL-C against cardiovascular disease. For example, in subjects with low HDL-C, administration of gemfibrozil results in a 6% increase in the HDL-C level and a corresponding 22% reduction of the CHD risk (Rubins et al. (1999) *N. Engl. J. Med.* 341, 410-418). Observations in genetic disorders associated with low HDL-C due to reduced ApoA-I expression, also indicate the link between elevated risk of CHD and low HDL-C.

HDL-C appears to exert its anti-atherogenic effect by mediating reverse cholesterol transport (RCT), in which cholesterol is recruited from peripheral tissues and transported to the liver. In addition, HDL-C also exerts anti-inflammatory and anti-oxidant effects and promotes fibrinolysis. HDL-C particles protect against oxidation of LDL, an important initial step in promoting cholesterol uptake by arterial macrophages. HDL-C exists in two main forms, one containing both apolipoprotein A-I (ApoA-I) and apolipoprotein A-II (ApoA-II), and the other containing ApoA-I without ApoA-II (Schultz et al. (1993) *Nature* 365, 762-764). The cardioprotective effect of HDL-C is mostly, but not exclusively, attributable to ApoA-I.

Clinical and experimental data suggest that the production of ApoA-I is a critical determinant of circulating HDL-C. For example, persons with familial hyperalphalipoproteinemia (elevated ApoA-I) appear to be protected from atherosclerosis, while those deficient in ApoA-I (hypoalphalipoproteinemia) show accelerated cardiovascular disease. In addition, various experimental manipulations to increase production of ApoA-I are associated with reduced atherogenicity. For example, human ApoA-I is protective in transgenic animal models (Shah et al. (1998) *Circulation* 97, 780-785; Rubin et al. (1991) *Nature* 353, 265-267), and treatment with ApoA-I$_{Milano}$ prevents atherosclerotic lesions and leads to regression of atherosclerotic plaques in human patients (Nissen et al. (2003) *JAMA* 290, 2292-2300). Further lines of research demonstrate that ApoA-I plays a role in enhancing reverse cholesterol transport, attenuating oxidative stress, increasing paraoxonase activity, enhancing anticoagulant activity, and increasing anti-inflammatory activity (Andersson (1997) *Curr. Opin. Lipidol.* 8, 225-228). Accordingly, ApoA-I is an attractive target for therapeutic intervention.

Currently available therapeutic agents that increase the plasma concentration of ApoA-I, for example, recombinant ApoA-I or peptides that mimic ApoA-I, have potential drawbacks with respect to, e.g., stability during storage, delivery of active product, and in vivo half-life. Thus, small molecule compounds that up-regulate the production of endogenous ApoA-I, such as, for example, up-regulators of ApoA-I expression, would be very attractive as new therapeutic agents for cardiovascular disease.

One class of compounds that are thought to contribute to the prevention of various diseases, including cancer and cardiovascular disease, is polyphenols. Polyphenols are present in most food and beverages of plant origin and are the most abundant dietary antioxidants (Scalbert & Williamson (2000) *J. Nutr.* 130, 2073S-2085S). However, the protective properties of polyphenols have not been fully realized due to poor bioavailability (Manach et al. (2005) *Am. J. Clin. Nutr.* 81, 230S-242S), lack of clinical significance in various reported studies assessing them (Williamson & Manach (2005) *Am. J. Clin. Nutr.* 81, 243S-255S), and deleterious effects at higher dose concentrations. For example, an abundant and available source of resveratrol, a well known stilbene polyphenol, is red wine (Wu et. al. (2001) *Int. J. Mol. Med.* 8, 3-17). However, red wine cannot be consumed in therapeutically efficacious quantities on a daily basis due to the numerous well documented deleterious effects of excessive alcohol consumption. The effects of resveratrol may be better or safer in the absence of alcohol.

Several human clinical studies involving the anti-oxidant effect of various polyphenols in various foods or beverages, have failed to demonstrate an unequivocal benefit with respect to primary clinical endpoints, such as oxidative stress, lipemia, and inflammation (Williamson & Manach (2005) *Am. J. Clin. Nutr.* 81, 243S-255S). For example, out of twelve recent intervention studies with differing polyphenol sources, six showed no effect on lipid parameters and six showed an improvement in the lipid parameters (Manach (2005) *Curr. Opin. Lipidol.* 16, 77-84). Such inconclusive data has limited the potential use of polyphenols, despite their many beneficial properties.

The use of naturally occurring polyphenols as potential therapeutics has also been impeded by the inability to achieve efficacious levels in the body, partly due to poor bioavailability (Manach et al., (2005) *Am. J. Clin. Nutr.* 81, 230S-242S). The bioavailability of any given polyphenol varies widely (from 1-26%) in different individuals. This variability is also seen with administration of different polyphenols to the same individual due to differences in absorption, metabolism, and excretion rates. For example, polyphenol flavonoids, such as quercetin, have been reported to have less than 1% intestinal absorption following oral administration (Gugler et al. (1975) *Eur. J. Clin. Pharm.* 9, 229-234). In addition, some polyphenol metabolites are known to negatively influence the biological activity of the parent compounds (Manach et al. (2005) *Am. J. Clin. Nutr.* 81, 230S-242S). Such metabolites often differ from the parent compound in terms of toxicity, efficacy, and length of residence in the plasma. Another limiting factor is the poor solubility of many polyphenols that limits the potential routes of administration. These and other factors have made it difficult to determine appropriate dosages of the naturally occurring polyphenols, naringenin or resveratrol, for use in humans.

Thus, there exists a need for polyphenol-like compounds to be developed as therapeutic agents for the treatment and prevention of cardiovascular disease and related diseases, particularly, cholesterol- or lipid-related disorders, such as, for example, atherosclerosis. It is therefore one of the objects of the present disclosure to provide compounds that up-regulate the expression of ApoA-I. In addition, the compounds may have more favorable pharmacological properties than naturally occurring polyphenols.

Cancer is a group of diseases caused by dysregulated cell proliferation. Therapeutic approaches aim to decrease the numbers of cancer cells by inhibiting cell replication or by inducing cancer cell differentiation or death, but there is still significant unmet medical need for more efficacious therapeutic agents. Cancer cells accumulate genetic and epigenetic changes that alter cell growth and metabolism in order to promote cell proliferation and increased resistance to programmed cell death, or apoptosis. Some of these changes include inactivation of tumor suppressor genes, activation of oncogenes, as well as modifications of the regulation of chromatin structure. Watson, *Cancer Discovery* 1:477-480 (2011); Morin et al., *Nature* 476:298-303 (2011).

Many modifications of histones in chromatin have been characterized, including acetylation at multiple lysines in histones H3 and H4. Peserico and Simone, *J. Biomed. Biotechnol.* 2011:371832 (2011). Histone acetylation is controlled by acetylases (HATs) as well as deacetylases (HDACs), and small molecule HDAC inhibitors have been developed with cancer as an indication. Hoshino and Matsubara, *Surg. Today* 40:809-815 (2010). Histone acetylation controls gene expression by recruiting protein complexes that bind directly to acetylated lysine via bromodomains. Sanchez and Zhou, *Curr. Opin. Drug Discov. Devel.* 12(5): 659-665 (2009). One such family, the bromodomain and extra terminal domain (BET) proteins, comprises Brd2, Brd3, Brd4, and BrdT each of which contains two bromodomains in tandem that can independently bind to acetylated lysines. Wu and Chiang, *J. Biol. Chem.* 282(18):13141-13145 (2007). BET proteins exert some of their effects on transcription by recruiting the positive transcription elongation factor b (p-TEFb), which stimulates transcription elongation by phosphorylating the C-terminal domain of RNA polymerase II and results in increased expression of growth promoting genes, such as, e.g., c-Myc and the well established cancer target Aurora B. Filippakopoulos et al., *Nature* 468:1067-1073 (2010).

Molecules that bind to BET proteins and prevent them from binding to chromatin, inhibit transcription and prevent cell replication, which is useful in cancer therapy and other settings. For example, it has been shown that BET proteins can be displaced from the chromatin by small molecule inhibitors, such as, e.g., JQ1, I-BET, and I-BET151, which specifically compete with the acetyl-lysine binding pocket of the BET protein bromodomains thereby preventing transcription elongation of their target genes. Filippakopoulos et al. (2010); Nicodeme et al., *Nature* 468:1119-1123 (2010); Dawson et al., *Nature* 478:529-533 (2011).

Inhibition of BET bromodomain-promoter interactions results in a subsequent reduction of myc transcription and protein levels. This results in $G_1$ arrest and extensive apoptosis in a variety of leukemia and lymphoma cell lines. Mertz et al., *PNAS* 108(40):16669-16674 (2011). The Myc family of proto-oncogenes (c-myc, l-myc, n-myc) is activated in 25-35% of all human cancers. Vita and Henrickson, *Seminars in Cancer Biol.* 16:318-330 (2006). Mouse models of cancer driven by overexpression of c-myc demonstrate that transiently inhibiting c-myc expression can cause tumor regression, cell death, and in some cancers such as leukemia, complete disease remission. Soucek et al., *Nature* 455:679-683 (2008). The absence of a clear ligand-binding domain of c-myc has made the development of an inhibitor a formidable challenge, thus alternative strategies to targeting c-myc transcription must be developed. Delmore et al., *Cell* 146:904-917 (2011). A mouse model of aggressive human medulloblastoma, in which c-myc is overexpressed, suggests that BET inhibitors may be useful for treating myc-amplified medulloblastoma. Kawauchi et al., *Cancer Cell* 21:168-180 (2012); Pei et al., *Cancer Cell* 21:155-167 (2012). Similarly, inhibition of n-myc through RNA interference significantly reduced tumor growth in neuroblastoma mouse models. Jiang et al., *Biochem. Biophs. Res. Commun.* 410:364-370 (2011). A similar role for l-myc was suggested in small cell lung carcinoma cell lines using antisense oligonucleotides to inhibit l-myc amplification. Dosaka-Akita et al., *Cancer Res.* 55:1559-1564 (1995). Therefore BET inhibitors have potential to be efficacious in treating multiple types of cancer.

In fact, small molecules that target the bromodomains of BET family members have demonstrated potential therapeutic use in treating cancer. See, e.g., Dawson et al. (2011), showing that a small molecule inhibitor of the BET family has a profound efficacy against human and murine mixed lineage leukemia (MLL)-fusion cell lines by early cell cycle arrest and apoptosis. Its mechanism of efficacy is the selective abrogation of Brd3/4 recruitment to chromatin. BET inhibitor JQ1 has demonstrated potent antitumor activity in murine xenograoft models of NUT (nuclear protein in testis) midline carcinoma (NMC), a rare but lethal form of cancer. NMC tumor cell growth is driven by a translocation of the Brd4 gene to the nutlin 1 gene. Filippakopoulos et al., (2010). JQ1 was also shown to be a potent antiproliferator in multiple myeloma, associated with cell cycle arrest and cellular senescence. Delmore et al. (2011).

BET inhibitors are also expected to be potential therapeutics for other types of cancer. For example, in acute myeloid leukemia (AML), Brd4 is required to sustain myc expression and continued disease progression. Zuber et al., *Nature* 478:524-8 (2011). Moreover, inactivation of Brd4 results in a rapid and drastic down-regulation of the transcription of the proto-oncogenes c-myc and n-myc in cell lines they are amplified. Dawson et al. (2011); Delmore et al. (2011); Zuber et al. (2011); Mertz et al. (2011). Consequently, treatment of tumors that have activation of c-myc with a BET inhibitor resulted in tumor regression through inactivation of c-myc transcription. BET inhibitors are also expected to have application in multiple myeloma, as the multiple myeloma SET domain (MMSET) which is implicated in this disease also binds to BET proteins. Dawson et al. (2011).

In addition to cancer, BET inhibitors are also expected to have anti-inflammatory and immunomodulatory properties. Lamotte et al., *Bioorganic & Med. Chem. Letters* (Feb. 24, 2012); Prinjha et al., *Trends Pharmacol. Sci.* 33(3):146-153 (2012). BET inhibitors I-BET and I-BET151 decrease IL-6 expression in vivo. I-BET was shown to confer protection against lipopolysaccharide-induced endotoxic shock and bacteria-induced sepsis and I-BET151 was shown to suppress bacterial-induced inflammation and sepsis in a murine model. Nicodeme et al. (2010); Lamotte et al. (2012). In addition, BET inhibitors may modulate responses to viral and bacterial infections, including HIV, herpes, and papilloma viruses.

The invention provides an immediate release formulation comprising, (i) a compound Formula I as an active ingredient

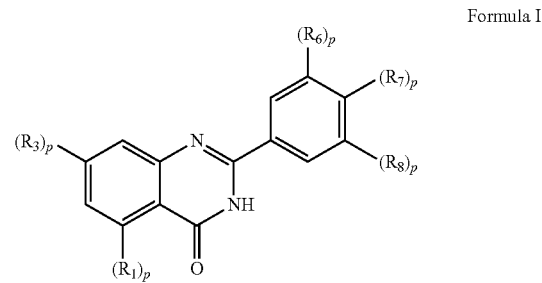

Formula I or a pharmaceutically acceptable salt, stereoisomer, hydrate, or tautomer thereof, wherein:

$R_1$ and $R_3$ are each independently selected from alkoxy, alkyl, and hydrogen;

$R_6$ and $R_8$ are each independently selected from alkoxy, alkyl, halogen, and hydrogen;

$R_7$ is selected from alkoxy, alkyl, ether, hydrogen, and hydroxyl; or two adjacent substituents selected from $R_1$, $R_3$, $R_6$, $R_7$, $R_8$, and are connected to form a group selected from aryl, heteroaryl, cycloalkyl, and heterocyclyl;

provided that if $R_1$ is hydrogen, then $R_3$ is alkoxy;
provided that if $R_3$ is hydrogen then $R_1$ is alkoxy; and
provided that if $R_7$ is selected from alkyl, hydroxyl, and alkoxy, then at least one of $R_6$ and $R_8$ are independently selected from alkyl or alkoxy;

(ii) at least one glidant; and
(iii) at least one disintegrant.

Important considerations during the manufacturing of a solid pharmaceutical formulation include preservation of the chemical and physical properties of the active ingredient, enhancement of bioavailability, ease of administration, and overall stability. In each case, the formulation must be based on the properties of the active/drug substance, balancing factors like disintegration, dissolution, particle size, size of unit, compatibility of components, and stability (see, e.g., The Pharmaceutical Codex, Principles and Practice of Pharmaceutics. Ed: Walter Lund; 2008, Ansel's Pharmaceutical Dosage Forms and Drug Delivery Systems, Lippincott Williams & Wilkins, 2010, Pharmaceutical Dosage forms: Tablets. Vol 1, 2. Eds: Liberman, Lachman and Schwartz. 2d edition).

Disintegration and dissolution are prerequisite steps for absorption, and the efficacy of these steps can affect the bioavailability of an active/drug substance. The solubility and thus the dissolution rate for weak acids and bases are influenced by the pH of the gastrointestinal fluids. For compounds that have reduced solubility in neutral and basic environments, like the small intestine, and a higher solubility at gastric pH, rapid disintegration and dissolution in the acidic gastric fluids may be critical for absorption in the small intestine (Principles of Drug Absorption, Michael Mayersohn. In *Modern Pharmaceutics Drugs and the Pharmaceutical Sciences, Vol 72*, edited by James Swarbrick).

Many active compounds, including compounds of Formula I, have poor aqueous solubility, thus reducing their potential for absorption from the gastrointestinal tract. A challenge to working with compounds having poor aqueous solubility is that it can be difficult to improve solubility without decreasing stability of the compound, thus reducing shelf life to an unacceptable levels. The hydrophobicity of compounds of Formula I can be altered when substituted with ionizable basic substituents, such as amines and/or amides, providing an opportunity for increased solubilization and absorption from the acidic gastric environment when dosed orally. However, due to the increasing pH gradient (pH 3 to 7) in the gastrointestinal cavity, the opportunity for dissolution and absorption is dependent on the rate of dissolution. As a result, if these compounds are not dissolved in the right gastric environment, absorption and bioavailability in the small intestine is reduced or lost. Thus, any improved biological activity gained from substituting compounds of Formula I with ionizable basic substitutents is compromised because of their diminished solubility in the small intestine, which leads to a decrease in the overall efficacy and therapeutic effects of the active drug substance.

Because compounds of Formula I have been shown to regulate expression of Apo-A1 and given the correlation between increased expression of Apo-A1 and treating or preventing cardiovascular and cholesterol- or lipid-related disorders, there is a need to develop solid pharmaceutical formulations comprising substituted quinazolinones, such as those described herein, where the pharmaceutical formulations improve dissolution of the quinazolinone drug substance, have favorable bioavailability, are convenient to administer, and which are stable for an extended period of time.

The invention provides novel solid pharmaceutical formulations comprising compounds of the Formula I, as defined above, and processes for their preparation. The formulations of the invention are stable and have improved disintegration and dissolution profiles for compounds of Formula I and improved bioavailability of the drug substance. The present invention also provides, in part, methods of using the pharmaceutical formulations of the invention that are useful for regulating the expression of apolipoprotein A-I (ApoA-I) and as BET inhibitors, for the treatment and prevention of cardiovascular disease, and cholesterol- or lipid-related disorders, including, for example, metabolic syndrome, inflammatory disease, Alzheimer's disease, atherosclerosis, diabetes, and cancer. Cancers that may be treated or prevented with the methods of the invention include cancers that are sensitive to a compound that binds to bromodomains of BET family proteins, including NUT midline carcinoma; cancers that exhibit c-myc overexpression, including, but not limited to, Burkitt's lymphoma, acute myelogenous leukemia, multiple myeloma, aggressive human medulloblastoma; cancers overexpressing n-myc; and cancers that rely on the recruitment of p-TEFb to regulate activated oncogenes such as, e.g., NOTCH1.

As used in this specification, the term "active ingredient" refers to a compound of Formula I. These compounds may be prepared as described in U.S. patent application Ser. No. 11/670,238 (U.S. Pat. No. 8,053,440), U.S. patent application Ser. No. 12/490,877 (U.S. Pat. No. 8,114,995), and U.S. Provisional Application No. 61/635,726, filed Apr. 19, 2012, incorporated herein by reference.

A dash ("-") that is not between two letters or symbols is used to indicate a point of attachment for a substituent. For example, —$CONH_2$ is attached through the carbon atom.

The expression "unit dosage form" as used herein, refers to a physically discrete unit of a pharmaceutical formulation appropriate for the subject to be treated. The total weight of a single unit dosage form, is determined by adding all the weights of the components in the unit dosage form, and does not include the weight of any coating(s) which may be applied to the unit dosage form or capsule that may be loaded with the unit dosage form. The total weight of a single unit dosage form is used as the basis for calculating the weight percentage of each of the components that comprise the unit dosage form.

As used herein, "w/w %" means by weight as a percentage of the total weight.

The term "about" is intended to mean approximately, in the region of, roughly, or around. When the term "about" is used in conjunction with a numerical range, it modifies that range by extending the boundaries above and below the numerical values set forth. In general, the term "about" is intended to modify a numerical value above and below the stated value by a variance of ≤10%.

Compounds of Formula I may exist as tautomers. It is intended that a description of any active ingredient, i.e., a compound of Formula I encompasses all tautomeric forms of the compound even if only one tautomeric structure is depicted or one compound name is recited. For example, any description of active ingredient A below is understood to equally represent tautomeric structures B and C, and vice versa, individually or as mixtures.

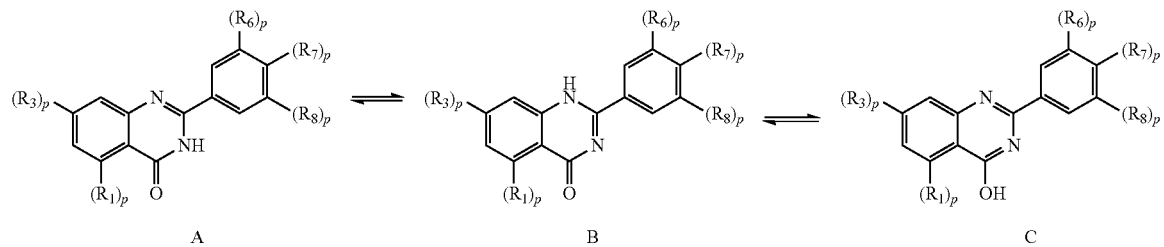

A  B  C

As used herein, the term "hydrate" refers to a crystal form of a compound of Formula I with either a stoichiometric or non-stoichiometric amount of water incorporated.

The term "alkoxy" as used herein refers to an alkyl group attached to an oxygen (—O-alkyl-). "Alkoxy" groups also include an alkenyl group attached to an oxygen ("alkenyloxy") or an alkynyl group attached to an oxygen ("alkynyloxy") groups. Exemplary alkoxy groups include, but are not limited to, groups with an alkyl, alkenyl or alkynyl group of 1-22, 1-8, or 1-6 carbon atoms, referred to herein as ($C_1$-$C_{22}$)alkoxy, ($C_1$-$C_8$)alkoxy, and ($C_1$-$C_6$)alkoxy, respectively. Exemplary alkoxy groups include, but are not limited to methoxy and ethoxy.

The term "alkyl" as used herein refers to a saturated straight or branched hydrocarbon, such as a straight or branched group of 1-22, 1-8, or 1-6 carbon atoms, referred to herein as ($C_1$-$C_{22}$)alkyl, ($C_1$-$C_8$)alkyl, and ($C_1$-$C_6$)alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl.

The term "aryl" as used herein refers to a mono-, bi-, or other multi-carbocyclic, aromatic ring system. The aryl group can optionally be fused to one or more rings selected from aryls, cycloalkyls, and heterocyclyls. The aryl groups of the compounds used in the formulations of the invention can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "($C_6$)aryl."

The term "cycloalkyl" as used herein refers to a saturated or unsaturated cyclic, bicyclic, or bridged bicyclic hydrocarbon group of 3-12 carbons, or 3-8 carbons, referred to herein as "($C_3$-$C_8$)cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl saturated or unsaturated, aryl, or heterocyclyl groups.

The term "ether" refers to the structure —$R_l$O—$R_m$—, where $R_l$ and $R_m$ can independently be alkyl, alkenyl, alkynyl, aryl, cycloalkyl, heterocyclyl, and ether. The ether can be attached to the parent molecular group through $R_l$ or $R_m$. Exemplary ethers include, but are not limited to, alkoxyalkyl and alkoxyaryl groups. Ethers also includes polyethers, e.g., where one or both of $R_l$ and $R_m$ are ethers.

The terms "halo" and "halogen" are interchangeable and refer to F, Cl, Br, or I.

The term "heteroaryl" as used herein refers to a mono-, bi-, or multi-cyclic, aromatic ring system containing one or more heteroatoms, for example 1-3 heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2-5 carbon atoms and 1-3 heteroatoms, referred to herein as "($C_2$-$C_5$)heteroaryl."

The terms "heterocycle," "heterocyclyl," or "heterocyclic" as used herein refer to a saturated or unsaturated 3-, 4-, 5-, 6-, or 7-membered ring containing one, two, or three heteroatoms independently selected from nitrogen, oxygen, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Heterocycles also include bicyclic, tricyclic, and tetracyclic groups in which any of the above heterocyclic rings is fused to one or two rings independently selected from aryl, cycloalkyl, and heterocycle. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

"Alkyl" groups can be substituted with or interrupted by or branched with at least one group selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, ketone, heteroaryl, heterocyclyl, hydroxyl, nitro, phosphate, sulfide, sulfinyl, sulfonyl, sulfonic acid, sulfonamide, thioketone, ureido, and N. The substituents may be branched to form a substituted or unsubstituted heterocycle or cycloalkyl.

"Alkoxy" groups can be substituted with or interrupted by or branched with at least one group selected from alkoxy, aryloxy, alkyl, alkenyl, alkynyl, amide, amino, aryl, arylalkyl, carbamate, carbonyl, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, thioketone, ureido, and N. The substituents may be branched to form a substituted or unsubstituted heterocycle or cycloalkyl.

The term "pharmaceutically acceptable salt(s)" refers to salts of acidic or basic groups that may be present in compounds of Formula I. Compounds of Formula I that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Compounds of Formula I that include an amino moiety may form pharmaceutically acceptable salts with various amino acids, in addition to the acids mentioned above. Compounds of Formula I that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

Compounds of Formula I may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. Compounds of Formula I encompass stereoisomers and mixtures thereof. Stereoisomers include enantiomers and diastereomers. Mixtures of enantiomers or diastereomers may be designated "(±)" in nomenclature, but the skilled artisan will recognize that a structure may contain an implicit chiral center.

Individual stereoisomers of compounds of Formula I can be prepared synthetically from commercially available starting materials that contain asymmetric or stereogenic centers, or by preparation of racemic mixtures followed by resolution methods well known to those of ordinary skill in the art. These methods of resolution include, but are not limited to (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well known methods, including, but not limited to chiral-phase gas chromatography, chiral-phase high performance liquid chromatography, crystallizing the compound as a chiral salt complex, and/or crystallizing the compound in a chiral solvent. Stereoisomers can also be obtained from stereomerically-pure intermediates, reagents, and catalysts by well known asymmetric synthetic methods.

Compounds of Formula I may also exist as geometric isomers or mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers.

Substituents around a carbon-carbon double bond alternatively can be referred to as "cis" or "trans," where "cis" represents substituents on the same side of the double bond and "trans" represents substituents on opposite sides of the double bond. The arrangements of substituents around a carbocyclic ring are designated as "cis" or "trans." The term "cis" represents substituents on the same side of the plane of the ring and the term "trans" represents substituents on opposite sides of the plane of the ring. Mixtures of compounds of Formula I wherein the substituents are disposed on both the same and opposite sides of plane of the ring are designated "cis/trans."

One exemplary embodiment of the invention is a pharmaceutical formulation comprising, as an active ingredient, a compound of Formula I wherein:

$R_1$ and $R_3$ are each independently selected from alkoxy, alkyl, and hydrogen;

$R_6$ and $R_8$ are each independently selected from alkyl, alkoxy, and hydrogen;

$R_7$ is selected from alkyl, hydroxyl, and alkoxy;

provided that if $R_1$ is hydrogen, then $R_3$ is alkoxy;

provided that if $R_3$ is hydrogen then $R_1$ is alkoxy; and provided that if $R_7$ is selected from alkyl, hydroxyl, and alkoxy, then at least one of $R_6$ and $R_8$ are independently selected from alkyl or alkoxy.

In one embodiment, formulations of the invention comprise, as an active ingredient, a compound of Formula I, wherein:

$R_1$ and $R_3$ are each alkoxy;

$R_6$ and $R_8$ are each alkyl; and $R_7$ is selected from alkoxy substituted with a hydroxyl.

In certain embodiments, formulations of the invention comprise, as an active ingredient, a compound of Formula I, wherein:

$R_1$ and $R_3$ are each methoxy;

$R_6$ and $R_8$ are each methyl; and $R_7$ is selected from alkoxy substituted with a hydroxyl.

In certain embodiments, formulations of the invention comprise an active ingredient wherein $R_7$ is selected from hydroxyl and alkoxy substituted with a hydroxyl. In other embodiments, $R_7$ is hydroxyl substituted with alkoxy. In further embodiments, $R_7$ is 2-hydroxyethoxy.

In some embodiments, the active ingredient is 2-(4-(2-hydroxyethoxy)-3,5-dimethylphenyl)-5,7-dimethoxyquinazolin-4(3H)-one or a pharmaceutically acceptable salt, stereoisomer, hydrate, or tautomer thereof.

In other embodiments, the active ingredient is the hydrochloride salt of 2-(4-(2-hydroxyethoxy)-3,5-dimethylphenyl)-5,7-dimethoxyquinazolin-4(3H)-one, or a stereoisomer or tautomer thereof.

In other embodiments, formulations of the invention comprise an active ingredient selected from:
2-(4-(2-hydroxyethoxy)-3,5-dimethylphenyl)quinazolin-4(3H)-one;
2-(3-chloro-4-(2-hydroxyethoxy)phenyl)-5,7-dimethoxyquinazolin-4(3H)-one;
2-(4-(2-hydroxyethoxy)-3-methoxyphenyl)-5,7-dimethoxyquinazolin-4(3H)-one;
2-(4-hydroxy-3-(2-hydroxyethyl)phenyl)-5,7-dimethoxyquinazolin-4(3H)-one;
2-(4-(2-hydroxyethoxy)-3,5-dimethylphenyl)-5,7-dimethylquinazolin-4(3H)-one;
2-(4-(2-hydroxyethoxy)-3,5-dimethylphenyl)-5-methoxyquinazolin-4(3H)-one, and
2-(4-(2-hydroxyethoxy)-3-methylphenyl)-5,7-dimethoxyquinazolin-4(3H)-one,
or a pharmaceutically acceptable salt, stereoisomer, hydrate, or tautomer thereof.

In certain embodiments, the pKa of the corresponding acid of the active ingredient of Formula I is <3. In some embodiments the particle size of the active ingredient ranges from about 1-250 microns, about 1-100 microns, or about 1-10 microns.

In certain embodiments, formulations of the invention are stable over extended periods of time. For example, in some embodiments, the formulations are stable for at least two years.

In some embodiments, the at least one glidant in the formulations of the invention is present an amount of 1-10% w/w, or 2-4% w/w, or 2.5% w/w. In some embodiments, the glidant is colloidal silicon dioxide such as, for example, Cab-O-Sil.

The at least one disintegrant in the formulations of the invention may be present in an amount of about 0-25% w/w, about 4-25% w/w, about 0-10% w/w, about 0-8% w/w, about 1-8% w/w, about 2-5% w/w, about 2-4% w/w, or about 4% w/w. In some embodiments, at least one disintegrant is present in an amount of about 4% w/w to about 25% w/w. Suitable disintegrants include, for example, powdered cellulose, calcium silicate, crospovidone, calcium alginate, methyl cellulose, chitosan, carboxy methyl cellulose, croscarmellose sodium, carboxymethyl starch, sodium alginate, sodium starch glycolate (e.g., ExploTab), pregelatinized starch, and mixtures thereof. See, e.g., The Pharmaceutical Codex, Principles and Practice of Pharmaceutics. Ed: Walter Lund; 2008.

In embodiments, formulations of the present disclosure comprise an active ingredient of the Formula I, colloidal silicon dioxide and at least one disintegrant selected from sodium starch glycolate, croscarmellose sodium, and mixtures thereof.

In certain embodiments, colloidal silicon dioxide is present in an amount of about 2.5% w/w and sodium starch glycolate and croscarmellose sodium are each present in an amount of about 4% w/w to about 25% w/w respectively.

In other embodiments, colloidal silicon dioxide is present in an amount of about 2.5% w/w and sodium starch glycolate is present in an amount of about 4% w/w.

In addition to the active ingredient, at least one glidant, and at least one disintegrant, the formulations may comprise one or more fillers or diluents. In some embodiments, the filler/diluent is present in an amount up to 85% w/w, or about 15-65% w/w, or about 20-45% w/w. Suitable fillers/diluents include, for example, microcrystalline cellulose, mannitol, ethyl cellulose, sorbitol, starch, sucrose, calcium phosphate, powdered cellulose, silicified microcrystalline cellulose, and mixtures thereof.

In some embodiments, the filler/diluent is microcrystalline cellulose. In certain embodiments, the microcrystalline cellulose is Avicel PH-301.

The formulations may further comprise one or more lubricants. In some embodiments, the lubricant is present in an amount of about 0-2% w/w, about 0-1% w/w, or about 0.5% w/w. Suitable lubricants include, for example, magnesium stearate, stearic acid, sodium stearyl fumarate, glyceryl behenate, hydrogenated vegetable oil, zinc stearate, calcium stearate, sucrose stearate, polyvinyl alcohol, magnesium lauryl sulfate, and mixtures thereof. In some embodiments, the lubricant is magnesium stearate.

The formulations of the invention may further comprise a surfactant. In some embodiments, the surfactant is present in an amount of about 0-5% w/w, about 0-3% w/w, or about 1% w/w. Suitable surfactants include, for example, sodium lauryl sulfate, sodium dodecyl sulfate, polysorbates (such as Tween 20 and Tween 80), poloxamers (such as Poloxamer 188), glyceryl monooleate, and mixtures thereof. In some embodiments, the surfactant is Poloxamer 188, sodium lauryl sulfate, and mixtures thereof.

In an exemplary embodiment of the invention, the pharmaceutical formulation comprises an active ingredient of Formula I, 10-85% microcrystalline cellulose, 1-8% sodium starch glycolate, 0.5-2% magnesium stearate, 1-10% colloidal silicon dioxide, 0-2% sodium lauryl sulfate, and 0-25% croscarmellose sodium.

In other embodiments, the formulation comprises an active ingredient of Formula I, 10-85% microcrystalline cellulose, 4% sodium starch glycolate, 0.5% magnesium stearate, and 2.5% colloidal silicon dioxide.

In certain embodiments, the formulation comprises an active ingredient of Formula I, 10-85% microcrystalline cellulose, 4% sodium starch glycolate, 25% croscarmellose sodium, 0.5% magnesium stearate, and 2.5% colloidal silicon dioxide.

In an exemplary embodiment, the formulation of the invention comprises:
(i) about 10-12% w/w 2-(4-(2-hydroxyethoxy)-3,5-dimethylphenyl)-5,7-dimethoxyquinazolin-4(3H)-one;
(ii) about 82-83% w/w Avicel PH 301;
(iii) about 2.5% w/w colloidal silicon dioxide;
(iv) about 4% w/w sodium starch glycolate; and
(v) about 0.5% w/w magnesium stearate.

In an alternate embodiment the hydrochloride salt of 2-(4-(2-hydroxyethoxy)-3,5-dimethylphenyl)-5,7-dimethoxyquinazolin-4(3H)-one may be substituted for 2-(4-(2-hydroxyethoxy)-3,5-dimethylphenyl)-5,7-dimethoxyquinazolin-4(3H)-one in this formulation.

In another exemplary embodiment, the formulation of the invention comprises:
(i) about 20-22% w/w 2-(4-(2-hydroxyethoxy)-3,5-dimethylphenyl)-5,7-dimethoxyquinazolin-4(3H)-one;
(ii) about 70-72% w/w Avicel PH 301;
(iii) about 2.5% w/w colloidal silicon dioxide;
(iv) about 4% w/w sodium starch glycolate; and
(v) about 0.5% w/w magnesium stearate.

In an alternate embodiment the hydrochloride salt of 2-(4-(2-hydroxyethoxy)-3,5-dimethylphenyl)-5,7-dimethoxyquinazolin-4(3H)-one may be substituted for 2-(4-(2-hydroxyethoxy)-3,5-dimethylphenyl)-5,7-dimethoxyquinazolin-4(3H)-one in this formulation.

In another exemplary embodiment, the formulation of the invention comprises:
(i) about 31-33% w/w 2-(4-(2-hydroxyethoxy)-3,5-dimethylphenyl)-5,7-dimethoxyquinazolin-4(3H)-one;
(ii) about 60-62% w/w Avicel PH 301;
(iii) about 2.5% w/w colloidal silicon dioxide;
(iv) about 4% w/w sodium starch glycolate; and
(v) about 0.5% w/w magnesium stearate.

In an alternate embodiment the hydrochloride salt of 2-(4-(2-hydroxyethoxy)-3,5-dimethylphenyl)-5,7-dimethoxyquinazolin-4(3H)-one may be substituted for 2-(4-(2-hydroxyethoxy)-3,5-dimethylphenyl)-5,7-dimethoxyquinazolin-4(3H)-one in this formulation.

In another exemplary embodiment, the formulation of the invention comprises:
(i) about 41-43% w/w 2-(4-(2-hydroxyethoxy)-3,5-dimethylphenyl)-5,7-dimethoxyquinazolin-4(3H)-one;
(ii) about 50-51% w/w Avicel PH 301;
(iii) about 2.5% w/w colloidal silicon dioxide;
(iv) about 4% w/w sodium starch glycolate; and
(v) about 0.5% w/w magnesium stearate.

In an alternate embodiment the hydrochloride salt of 2-(4-(2-hydroxyethoxy)-3,5-dimethylphenyl)-5,7-dimethoxyquinazolin-4(3H)-one may be substituted for 2-(4-(2-hydroxyethoxy)-3,5-dimethylphenyl)-5,7-dimethoxyquinazolin-4(3H)-one in this formulation.

In another exemplary embodiment, the formulation of the invention comprises:
(i) about 10-12% w/w 2-(4-(2-hydroxyethoxy)-3,5-dimethylphenyl)-5,7-dimethoxyquinazolin-4(3H)-one or a hydrochloride salt thereof;
(ii) about 56-57% w/w Avicel PH 301;
(iii) about 2.5% w/w colloidal silicon dioxide;
(iv) about 4% w/w sodium starch glycolate;
(v) about 0.5% w/w magnesium stearate; and
(vi) about 25% w/w croscarmellose sodium.

In an alternate embodiment the hydrochloride salt of 2-(4-(2-hydroxyethoxy)-3,5-dimethylphenyl)-5,7-dimethoxyquinazolin-4(3H)-one may be substituted for 2-(4-(2-hydroxyethoxy)-3,5-dimethylphenyl)-5,7-dimethoxyquinazolin-4(3H)-one in this formulation.

In another exemplary embodiment, the formulation of the invention comprises:
(i) about 42-43% w/w 2-(4-(2-hydroxyethoxy)-3,5-dimethylphenyl)-5,7-dimethoxyquinazolin-4(3H)-one or a hydrochloride salt thereof;
(ii) about 24-25% w/w Avicel PH 301;
(iii) about 2.5% w/w colloidal silicon dioxide;
(iv) about 4% w/w sodium starch glycolate;
(v) about 0.5% w/w magnesium stearate;
(vi) about 25% w/w croscarmellose sodium; and
(vii) about 1% w/w sodium lauryl sulfate.

In an alternate embodiment the hydrochloride salt of 2-(4-(2-hydroxyethoxy)-3,5-dimethylphenyl)-5,7-dimethoxyquinazolin-4(3H)-one may be substituted for 2-(4-(2-hydroxyethoxy)-3,5-dimethylphenyl)-5,7-dimethoxyquinazolin-4(3H)-one in this formulation.

The physical and chemical stability of the formulation may be tested in a conventional manner, for example, the measurement of dissolution or disintegration time, or moisture content, or assay for the active ingredient or degradation products after storage at different temperatures and relative humidity for different lengths of time.

The pharmaceutical formulations of the invention may be administered using any amount effective for treating the disease. The exact amount required will vary from subject to subject, depending on the species, age, and general condition of the subject, the severity of the disease and/or disorder, the particular active ingredient, its mode of administration, and the like. In one aspect, the pharmaceutical formulations are formulated in an oral pharmaceutical unit dosage form for ease of administration and uniformity of dosage. It will be understood, however, that the total daily usage of the pharmaceutical formulation of the present invention will be decided by the attending physician within the scope of sound medical judgment.

The specific effective dose level for any particular subject will depend on a variety of factors including, for example, the disease being treated and the severity of the disease; the activity of the specific compound employed; the specific composition employed; the age, body weight, general health, gender, and diet of the subject; the time of administration, and rate of excretion of the specific compound employed; the duration of the treatment; drugs used in combination or coincidental with the specific compound employed, and like factors well known in the medical arts.

In some embodiments, the unit dosage form comprises between 25-150 mg of the active pharmaceutical ingredient. In some embodiments, the unit dosage form comprises about 25, 50, 75, 100 or 150 mg of the active pharmaceutical ingredient.

In one embodiment, the present disclosure provides for pharmaceutical formulations in solid oral pharmaceutical dosage forms. Examples of solid oral pharmaceutical dosage forms include, for example, tablets, capsules, pills, powders, and granules. In certain embodiments, the pharmaceutical formulation is in the form of a capsule. While formulations of the invention are described with reference to capsules as the exemplary dosage form, other dosage forms are also within the scope of this invention.

In some embodiments, the capsules are filled with a total weight between 100 and 500 mg per capsule. In some embodiments, the capsules are filled with a total weight of about 200-250 mg per capsule; and in some embodiments, the capsules are filled with a total weight of about 230 mg per capsule.

As used herein, the term "cardiovascular disease" refers to diseases and disorders of the heart and circulatory system. Exemplary cardiovascular diseases, including cholesterol- or lipid-related disorders, include, but are not limited to acute coronary syndrome, angina, arteriosclerosis, atherosclerosis, carotid atherosclerosis, cerebrovascular disease, cerebral infarction, congestive heart failure, congenital heart disease, coronary heart disease, coronary artery disease, coronary plaque stabilization, dyslipidemias, dyslipoproteinemias, endothelium dysfunctions, familial hypercholesterolemia, familial combined hyperlipidemia, hypoalphalipoproteinemia, hypertriglyceridemia, hyperbetalipoproteinemia, hypercholesterolemia, hypertension, hyperlipidemia, intermittent claudication, ischemia, ischemia reperfusion injury, ischemic heart diseases, cardiac ischemia, metabolic syndrome, multi-infarct dementia, myocardial infarction, obesity, peripheral vascular disease, reperfusion injury, restenosis, renal artery atherosclerosis, rheumatic heart disease, stroke, thrombotic disorder, transitory ischemic attacks, and lipoprotein abnormalities associated with Alzheimer's disease, obesity, diabetes mellitus, syndrome X, impotence, multiple sclerosis, Parkinson's diseases and inflammatory diseases.

Diseases and conditions associated with "diabetes mellitus" as defined herein refer to chronic metabolic disorder(s) caused by absolute or relative insulin deficiency including, but not limited to hyperglycemia, hyperinsulinemia, hyperlipidemia, insulin resistance, impaired glucose metabolism, obesity, diabetic retinopathy, macular degeneration, cataracts, diabetic nephropathy, glomerulosclerosis, diabetic neuropathy, erectile dysfunction, premenstrual syndrome, vascular restenosis, ulcerative colitis, skin and connective tissue disorders, foot ulcerations, metabolic acidosis, arthritis, osteoporosis and impaired glucose tolerance.

In certain embodiments, the cancer to be treated is a midline carcinoma. In some embodiments, the cancer is characterized by c-myc activation or overexpression. In other embodiments, the cancer is characterized by overexpression or activation of n-myc. In certain embodiments, the cancer is Burkitt's lymphoma, acute myelogenous leukemia, multiple myeloma, or aggressive human medulloblastoma. In some embodiments, the cancer relies on the recruitment of p-TEFb to regulate activated oncogenes such as, e.g., NOTCH1. In some embodiments, the cancer to be treated or prevented by the methods of the invention is selected from the group consisting of hematological, epithelial including lung, breast and colon carcinomas, midline carcinomas, mesenchymal, hepatic, renal and neurological tumours.

The certain embodiments, administration of a compound of Formula I or Formula II or a tautomer, stereoisomer, pharmaceutically acceptable salt or hydrate thereof, to a mammal suffering from a cancer induces apoptosis in cancer cells by decreasing expression of the anti-apoptosis gene Bcl2. Thus, some embodiments of the invention provide a method of treating or preventing a disease or disorder in a mammal that benefits from increased cell death or differentiation, or decreased cell proliferation, comprising administering a compound of Formula I or Formula II or a tautomer, stereoisomer, pharmaceutically acceptable salt or hydrate thereof.

The invention is further illustrated by the following non-limiting examples.

EXAMPLES 2-(4-(2-hydroxyethoxy)-3,5-dimethylphenyl)-5,7-dimethoxyquinazolin-4(3H)-one (Compound 1) was prepared according to the synthetic methods described in U.S. patent application Ser. Nos. 11/670,238 and 12/490,877, incorporated herein by reference.

Capsules containing formulations of the invention may be produced using any suitable apparatus or procedure. Typically, the appropriate amount of the active pharmaceutical ingredient and optionally, sodium starch glycolate are weighed out and transferred to a V-blender or bin-blender and blended, for example, for about 2 min at about 25 rpm. Colloidal silicon oxide and approximately ⅓ of the desired amount of a filler/diluent, such as microcrystalline cellulose are screened and added to the same V-blender, and the ingredients are blended for about 2 min at about 25 rpm. The remaining filler/diluent, such as microcrystalline cellulose is added to the same V-blender, and the ingredients are blended for about 4 min at about 25 rpm.

A lubricant, such as magnesium stearate, is screened through a 30 mesh screen and transferred to the V-blender containing the other ingredients. The final formulation is blended for about 3 min at about 25 rpm.

Disintegration of capsules was monitored visually during the first 5 min while conducting dissolution testing, as seen by bursting of the capsule to release and disperse the formulation blend from the capsule shell. Dissolution testing was conducted in a USP Paddle type II apparatus at 50 and/or 75 rpm in 0.1 N HCl at 37° C. The dissolution profile of the formulations were determined by sampling the API released from the formulation in the dissolution media at frequent time points, such as 5, 10, 15, 30, 45, 60, and 90 min. Samples were assayed for drug content by HPLC and a dissolution profile was generated. For these experiments, the upper threshold for dissolution profiles included those which exhibited >85% drug released in 30 min or less, at 75 rpm paddle speed. A lower paddle speed (50 rpm) was used to differentiate dissolution performance of closely performing formulations.

Considering factors such as, for example, number of excipients, density of blend, stability, and scaleability, the numerous formulations were produced at various API weight percentages. The following formulations provided higher levels of drug load and a higher density leading to increased manufacturability, reducing the exposure of inactive ingredients to subjects. In addition, the combination of two or more disintegrants in conjunction with high levels of glidant (e.g., silicon dioxide) improved disintegration and dissolution profiles.

Formulation D4 (25 mg/capsule)

| Ingredients | mg/capsule | % wt./wt |
|---|---|---|
| Compound 1 | 25.00 | 10.73 |
| Microcrystalline cellulose (Avicel PH 301) | 191.69 | 82.27 |
| Colloidal silicon dioxide (Cab-O-Sil M5P) | 5.83 | 2.5 |
| Sodium starch glycolate (ExploTab) | 9.32 | 4.0 |
| Magnesium stearate (Vegetable Source) | 1.17 | 0.5 |
| Hard shell gelatin capsule white/white Size 1 Capsugel | — | — |
| Total | 233.01 | 100.0 |

Formulation D4 (50 mg/capsule)

| Ingredients | mg/capsule | % wt./wt |
|---|---|---|
| Compound 1 | 50 | 21.46 |
| Microcrystalline cellulose (Avicel PH 301) | 166.69 | 71.54 |
| Colloidal silicon dioxide (Cab-O-Sil M5P) | 5.83 | 2.5 |
| Sodium starch glycolate (ExploTab) | 9.32 | 4.0 |
| Magnesium stearate (Vegetable Source) | 1.17 | 0.5 |
| Hard shell gelatin capsule white/white Size 1 Capsugel | — | — |
| Total | 233.01 | 100.0 |

Formulation D4 (75 mg/capsule)

| Ingredients | mg/capsule | % wt./wt |
|---|---|---|
| Compound 1 | 75.00 | 32.19 |
| Microcrystalline cellulose (Avicel PH 301) | 141.69 | 60.81 |

-continued

| Ingredients | mg/capsule | % wt./wt |
|---|---|---|
| Colloidal silicon dioxide (Cab-O-Sil M5P) | 5.83 | 2.5 |
| Sodium starch glycolate (ExploTab) | 9.32 | 4.0 |
| Magnesium stearate (Vegetable Source) | 1.17 | 0.5 |
| Hard shell gelatin capsule white/white Size 1 Capsugel | — | — |
| Total | 233.01 | 100.0 |

Formulation D4 (100 mg/capsule)

| Ingredients | mg/capsule | % wt./wt |
|---|---|---|
| Compound 1 | 100.00 | 42.9 |
| Microcrystalline cellulose (Avicel PH 301) | 116.69 | 50.1 |
| Colloidal silicon dioxide (Cab-O-Sil M5P) | 5.83 | 2.5 |
| Sodium starch glycolate (ExploTab) | 9.32 | 4.0 |
| Magnesium stearate (Vegetable Source) | 1.17 | 0.5 |
| Hard shell gelatin capsule white/white Size 1 Capsugel | — | — |
| Total | 233.01 | 100.0 |

Formulation F3 (25 mg/capsule)

| Ingredients | mg/capsule | % wt./wt |
|---|---|---|
| Compound 1 | 25.00 | 10.73 |
| Microcrystalline cellulose (Avicel PH 301) | 197.0 | 56.29 |
| Colloidal silicon dioxide (Cab-O-Sil M5P) | 5.83 | 2.5 |
| Sodium starch glycolate (ExploTab) | 9.32 | 4.0 |
| Magnesium stearate (vegetable source) | 1.17 | 0.5 |
| Croscarmellose sodium | 58.25 | 25 |
| Hard shell gelatin capsule white/white Size 1 Capsugel | — | — |
| Total | 233.01 | 100.0 |

Formulation F3" (100 mg/capsule)

| Ingredients | mg/capsule | % wt./wt |
|---|---|---|
| Compound 1 | 100 | 42.9 |
| Microcrystalline cellulose (Avicel PH 301) | 56.25 | 24.14 |
| Colloidal silicon dioxide (Cab-O-Sil M5P) | 5.83 | 2.5 |
| Sodium starch glycolate (ExploTab) | 9.32 | 4.0 |
| Magnesium stearate (Vegetable Source) | 1.17 | 0.5 |
| Croscarmellose sodium | 58.25 | 25 |
| Sodium lauryl sulfate | 2.33 | 1 |
| Hard shell gelatin capsule white/white Size 1 Capsugel | — | — |
| Total | 233.01 | 100.0 |

Of the formulations above, D4 had the fewest inactive ingredients, and thus, the highest levels of drug load and density, thereby reducing unnecessary exposure to inactive ingredients. Dissolution profiles of the formulations above are provided in Table 1.

TABLE 1

Dissolution Results

| Capsule Strength (mg) | Formulation | Paddle Speed RPM | % Compound 1 Dissolved (Average of 3 vessels) | | |
|---|---|---|---|---|---|
| | | | 15 | 30 | 45 |
| 200 (used 2 caps) | F3 | 50 | 59.84 | 64.10 | 66.15 |
| 200 (used 2 caps) | F3" | 50 | 62.83 | 66.79 | 69.65 |
| 200 (used 2 caps) | D4 | 50 | 53.09 | 66.08 | 74.05 |

Thus, the present disclosure provides in part, a technical solution to the existing problem of developing formulations that increase the bioavailability of compounds of Formula I, while preserving compound stability and shelf-life. Because of the known ability of compounds of Formula I to regulate expression of ApoA-1 and as BET inhibitors, the aforementioned immediate release formulations also provide an avenue for the treatment and prevention of cardiovascular disease, and cholesterol- or lipid-related disorders, including, for example, metabolic syndrome, inflammatory disease, Alzheimer's disease, atherosclerosis, diabetes, and cancer.

What is claimed is:
1. A pharmaceutical formulation comprising an active ingredient selected from:
   2-(4-(2-hydroxyethoxy)-3,5-dimethylphenyl)-5,7-dimethoxyquinazolin-4(3H)-one;
   and pharmaceutically acceptable salts, stereoisomers, hydrates, and tautomers thereof;
wherein the active ingredient is present:
   (a) in an amount from about 10% to about 12% by weight and the formulation further comprises:
      (i) about 82% to about 83% by weight of microcrystalline cellulose;
      (ii) about 2.5% by weight of colloidal silicon dioxide;
      (iii) about 4.0% by weight of sodium starch glycolate; and
      (iv) about 0.5% by weight of magnesium stearate;
   (b) in an amount from about 20% to about 22% by weight and the formulation further comprises:
      (i) about 70% to about 72% by weight of microcrystalline cellulose;
      (ii) about 2.5% by weight of colloidal silicon dioxide;
      (iii) about 4.0% by weight of sodium starch glycolate; and
      (iv) about 0.5% by weight of magnesium stearate;
   (c) in an amount from about 31% to about 33% by weight and the formulation further comprises:
      (i) about 60% to about 62% by weight of microcrystalline cellulose;
      about 2.5% by weight of colloidal silicon dioxide;
      (iii) about 4.0% by weight of sodium starch glycolate; and
      (iv) about 0.5% by weight of magnesium stearate;
   or
   (d) in an amount from about 41% to about 43% by weight and the formulation further comprises:
      (1) about 50% to about 51% by weight of microcrystalline cellulose;
      (ii) about 2.5% by weight of colloidal silicon dioxide;
      (iii) about 4.0% by weight of sodium starch glycolate; and
      (iv) about 0.5% by weight of magnesium stearate;

and wherein the formulation is formulated for oral administration and immediate release.

2. The formulation of claim 1, wherein the active ingredient is 2-(4-(2-hydroxyethoxy)-3,5-dimethylphenyl)-5,7-dimethoxyquinazolin-4(3H)-one.

3. The formulation of claim 1, wherein the active ingredient is the hydrochloride salt of 2-(4-(2-hydroxyethoxy)-3,5-dimethylphenyl)-5,7-dimethoxyquinazolin-4(3H)-one.

4. The formulation of claim 1, wherein the active ingredient has a particle size from about 1-250 microns, about 1-100 microns, or about 1-10 microns.

5. The formulation of claim 1, wherein the formulation comprises from about 25-100 mg of the active ingredient.

6. The formulation of claim 5, wherein the active ingredient is present in the formulation in an amount selected from about 25, 50, 75, or 100 mg.

7. The formulation of claim 1, wherein the formulation has a disintegration time of 120 seconds or less.

\* \* \* \* \*